(12) United States Patent
Van Rensburg et al.

(10) Patent No.: US 12,396,740 B2
(45) Date of Patent: Aug. 26, 2025

(54) NAVIGATION-GUIDED SURGERY FIXATION (NGSF) KIT OR SYSTEM AND METHOD OF USING SAME

(71) Applicant: DDS Company, Inc., Durham, NC (US)

(72) Inventors: Cornelis J. Janse Van Rensburg, Durham, NC (US); Matthew Vrhovac, Durham, NC (US); Richard Meaney, Durham, NC (US); Louis Costanzo, Durham, NC (US)

(73) Assignee: DDS Company, Inc., Durham, NC (US)

(*) Notice: Subject to any disclaimer, the term of this patent is extended or adjusted under 35 U.S.C. 154(b) by 590 days.

(21) Appl. No.: 17/847,304

(22) Filed: Jun. 23, 2022

(65) Prior Publication Data

US 2022/0409220 A1   Dec. 29, 2022

Related U.S. Application Data

(60) Provisional application No. 63/213,985, filed on Jun. 23, 2021.

(51) Int. Cl.
*A61B 17/17*   (2006.01)
*A61B 17/56*   (2006.01)
*A61B 17/86*   (2006.01)

(52) U.S. Cl.
CPC ...... *A61B 17/176* (2013.01); *A61B 2017/564* (2013.01)

(58) Field of Classification Search
CPC ... A61B 17/176; A61B 17/86; A61B 17/8605; A61C 1/082
See application file for complete search history.

(56) References Cited

U.S. PATENT DOCUMENTS

| | | | |
|---|---|---|---|
| 4,142,517 A * | 3/1979 | Contreras Guerrero de Stavropoulos | A61B 10/025 606/179 |
| 5,139,520 A * | 8/1992 | Rosenberg | A61B 17/1714 606/87 |
| 5,967,777 A * | 10/1999 | Klein | A61C 9/0053 433/76 |
| 8,574,236 B2 * | 11/2013 | Sawatari | A61F 2/2803 433/215 |
| 10,376,206 B2 * | 8/2019 | Sand | A61B 5/6847 |
| 2007/0049945 A1 * | 3/2007 | Miller | A61B 17/3476 606/86 R |
| 2009/0112208 A1 * | 4/2009 | Borgia | A61B 17/16 606/301 |
| 2010/0094356 A1 * | 4/2010 | Varela | A61B 17/8605 606/304 |

(Continued)

*Primary Examiner* — Nicholas W Woodall
(74) *Attorney, Agent, or Firm* — Ward and Smith, P.A.; Ryan K. Simmons

(57) ABSTRACT

A navigation-guided surgery fixation (NGSF) system. The NGSF system may include a fixation member for fixating an intraoral surgical guide. The fixation member may include a shank portion and a shaft portion, the shaft portion extending out from an end portion of the shank portion, and wherein the shank portion has a diameter greater than that of the shaft portion; and a sleeve member, wherein the sleeve member may include a through-hole substantially the same size of the shank portion and configured to receive the shank portion therein.

10 Claims, 28 Drawing Sheets

(56) References Cited

U.S. PATENT DOCUMENTS

2015/0164518 A1* 6/2015 Jinton .............. A61B 17/685
606/86 R

* cited by examiner

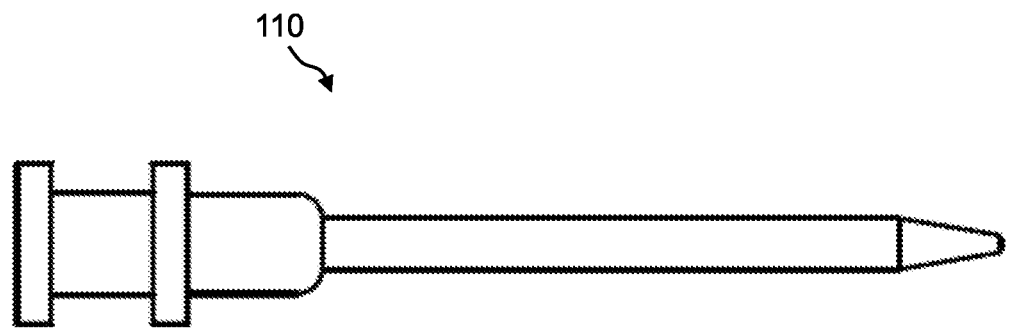
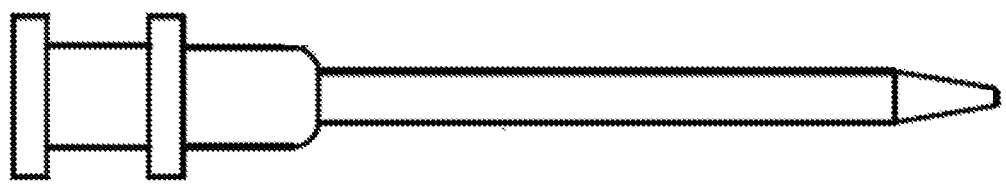
FIG. 7

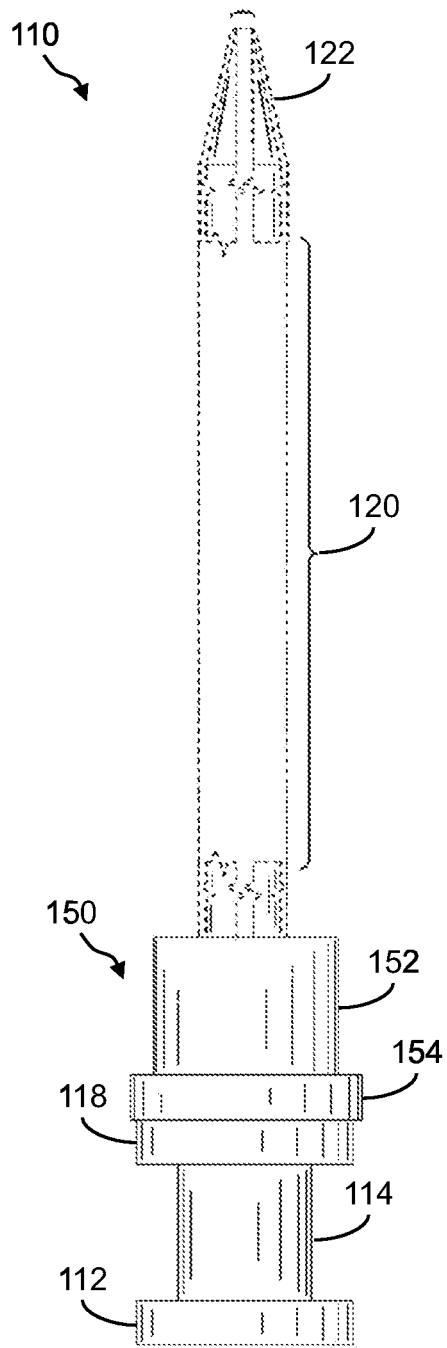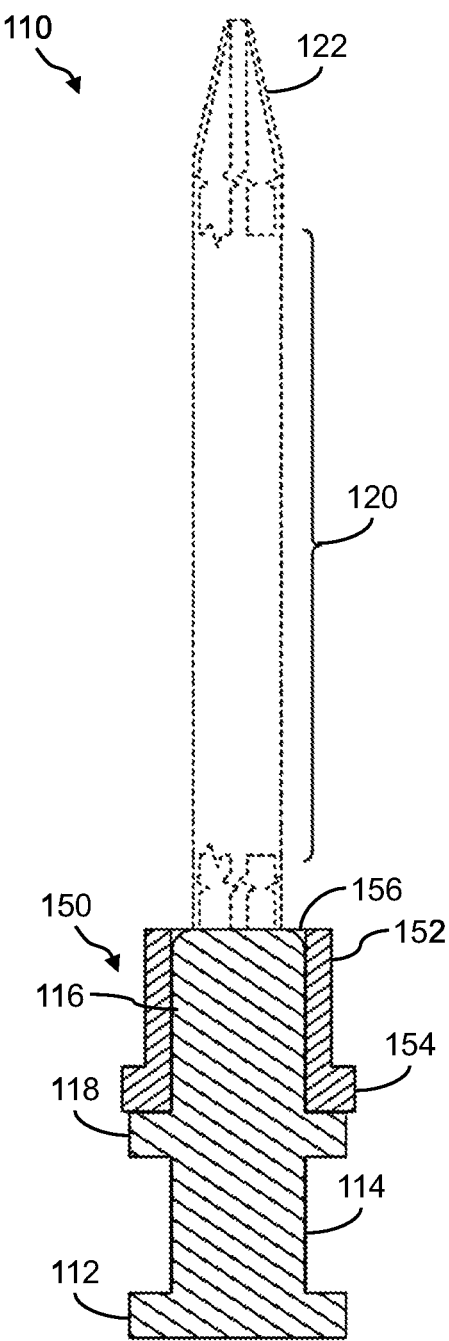
*FIG. 20A*　　　*FIG. 20B*

NAVIGATION-GUIDED SURGERY FIXATION (NGSF) KIT OR SYSTEM AND METHOD OF USING SAME

RELATED APPLICATIONS

This application is related and claims priority to U.S. Provisional Patent Application No.: 63/213,985, filed on Jun. 23, 2021, the application of which is incorporate herein by reference in its entirety.

TECHNICAL FIELD

The presently disclosed subject matter relates generally to systems and methods for performing intraoral guided surgery and more particularly to a navigation-guided surgery fixation (NGSF) kit or system and method of using same.

BACKGROUND

Currently, intraoral guided surgery procedures, such as, but not limited to, bone fixated (bone touching/contacting) guide-assisted surgical procedures, utilize surgical fixation kits for screw or pin fixation. Current surgical fixation kits have proven suitable for intraoral guided surgery at its present state of evolution. However, the next generation of surgical guides will require no tissue reflection for guide seating. This evolution will encounter several shortcomings in the stability and useable angle of current guide fixation systems.

In one example, over the course of a surgery, fixation pins may loosen in the bone causing a loss of guide stability at critical points during surgery. For example, seating the temporary prosthetic is the last step in the use of these surgical guides. A loss of pin stability will require excessive time spent adjusting the temporary prosthetic to fit. Additionally, if the loosening of the pins is severe enough, it can lead to abandonment of the entire surgical kit all together. This results in lengthening the total procedure time and reducing the precision of the overall surgical procedure. Currently fixation kits provide no solution to this shortcoming, such as an option to replace a fixation pin with one of different diameter during surgery, which would allow a guide to be "re-secured" when fixation comes loose.

Additionally, current drills intended for piloting at fixation sites have a limitation in angle of approach to the bone. Excessive approach angles may cause the drill to wander and effect accuracy, resulting in an incorrectly seated guide. Accordingly, new approaches are needed with respect to performing intraoral guided surgery procedures that utilize surgical fixation kits.

SUMMARY

In one embodiment, a navigation-guided surgery fixation (NGSF) system is provided. The NGSF system may include a fixation member for fixating an intraoral surgical guide. The fixation member may include a shank portion and a shaft portion, the shaft portion extending out from an end portion of the shank portion, and wherein the shank portion has a diameter greater than that of the shaft portion; and a sleeve member, wherein the sleeve member may include a through-hole substantially the same size of the shank portion and configured to receive the shank portion therein. The fixation member may include at least one of a fixation pin or a fixation screw. The fixation member may further include a head portion at a proximal end of the fixation member; a baseplate portion spaced apart from the head portion; a spacer portion disposed between the head portion and the baseplate portion; a tip portion at a distal end of the shaft portion; and wherein the shank portion extends out at its proximal end from a side of the baseplate opposite that of the spacer. The sleeve member may further include a sleeve body; and a sleeve baseplate. The sleeve body may be configured to fit within a fixation guide hole of the intraoral surgical guide. The system may further include a fixation drill key, the fixation drill key may include a through-hole, wherein at least a portion of the fixation drill key is configured to be received within the through-hole of the sleeve member; and a fixation drill bit, wherein at least a portion of the fixation drill bit is configured to be received through the through-hole of the fixation drill key. The fixation drill key may further include a drill key body; a drill key arm extending out perpendicularly from a side of the drill key body; and a drill key shank extending from a surface of the drill key body and substantially perpendicular to the drill key arm, and wherein the through-hole of the fixation drill key extends through both the drill key body and the drill key shank. The fixation drill bit may include a drill bit shank; and a drill bit, the drill bit extending out from the drill bit shank, wherein the drill bit portion is configured to be at least partially received through the sleeve member through-hole and the fixation drill key through-hole.

In another embodiment, a navigation-guided surgery fixation (NGSF) kit is provided. The NGSF kit may include a plurality of fixation members, each of which may include a shank portion and a shaft portion extending out from an end portion of the shank portion, wherein the shank portions of all of the plurality of fixation members have a same diameter which is greater than a diameter of any one of the shaft portions of the plurality of fixation members, and wherein the shaft portions of one or more of the plurality of fixation members have differing diameters from one another. The NGSF kit may further include a sleeve member, wherein the sleeve member may include a through-hole having a diameter substantially the same as that of the shank portion of the plurality of fixation members and is configured to receive the shank portion of the plurality of fixation members therein. The fixation members may include at least one of a fixation pin or a fixation screw. The NGSF kit may further include a fixation drill key, the fixation drill key may include a through-hole, wherein at least a portion of the fixation drill key is configured to be received within the through-hole of the sleeve member; and a fixation drill bit, wherein at least a portion of the fixation drill bit is configured to be received through the through-hole of the fixation drill key.

In yet another embodiment, a method of using navigation-guided surgery fixation (NGSF) kit is provided. The method may include providing a NGSF kit. The NGSF kit may include a plurality of fixation members, each of which may include a shank portion and a shaft portion extending out from an end portion of the shank portion, wherein the shank portions of all of the plurality of fixation members have a same diameter which is greater than a diameter of any one of the shaft portions of the plurality of fixation members, and wherein the shaft portions of one or more of the plurality of fixation members have differing diameters from one another; a sleeve member, wherein the sleeve member may include a through-hole having a diameter substantially the same as that of the shank portion of the plurality of fixation members and is configured to receive the shank portion of the plurality of fixation members therein; a fixation drill key, wherein a portion of the fixation drill key is configured to be received within the through-hole of the sleeve member; and a fixation drill bit, wherein at least a portion of the fixation drill bit is configured to be received through at least a portion of the through-hole of the fixation drill key. The method may further include positioning an intraoral surgical guide in a patient's oral cavity; engaging the fixation drill bit with the sleeve member using the fixation drill key, wherein at least a portion of the sleeve member is fitted into a fixation guide hole of the intraoral surgical guide prior to engaging the fixation drill bit with the sleeve member; drilling one or more fixation/pilot holes in the patient's oral cavity; removing the fixation drill bit from the patient's oral cavity; inserting one of the plurality of fixation members into the through-hole of the sleeve member aligned with the drilled fixation/pilot hole such that the shank portion of the fixation member is fitted into the through-hole of the sleeve member; fixating the inserted fixation member to bone tissue of the patient's oral cavity; determining whether or not the fixation of the inserted fixation member has loosened; and if determined the fixation of the inserted fixation member has loosened, removing the loosened fixation member and installing a fixation member comprising a larger diameter shaft portion. The plurality of fixation member may include at least one of a fixation pin or a fixation screw. The fixation drill bit may be engaged with the sleeve member using the fixation drill key, and wherein at least a portion of the fixation drill key may be fitted into the through-hole of the sleeve member to guide the fixation drill. The method may further include removing the fixation drill key from the sleeve member and patient's oral cavity.

BRIEF DESCRIPTION OF THE DRAWINGS

Figure 1A:
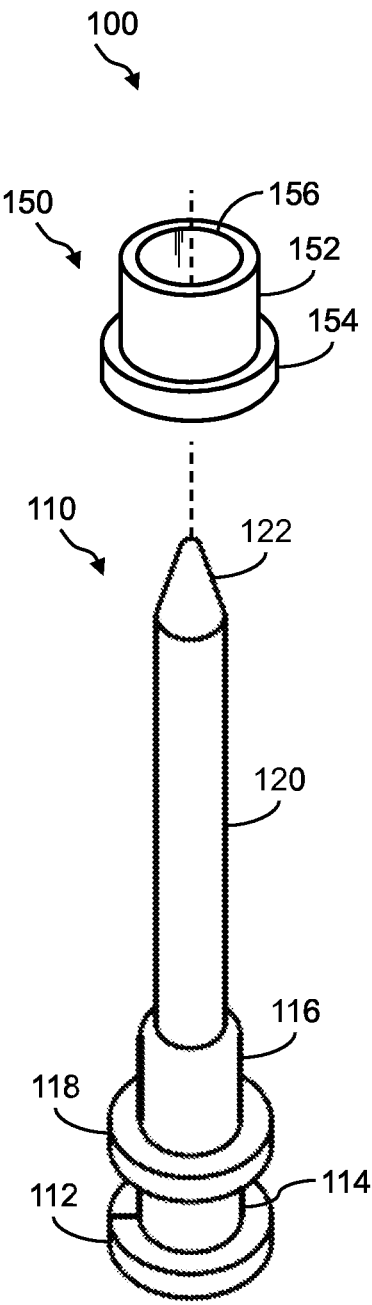
Figure 1B:
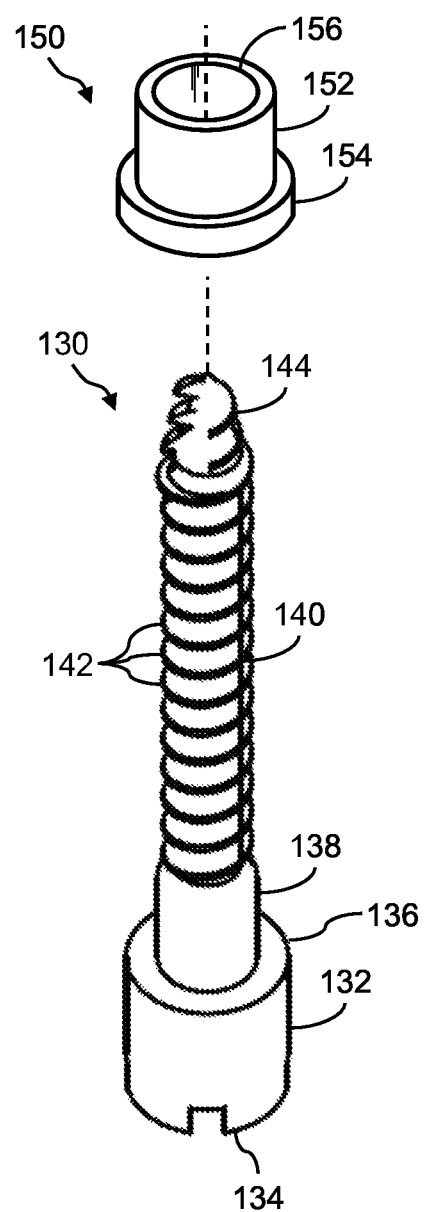
Figure 2:
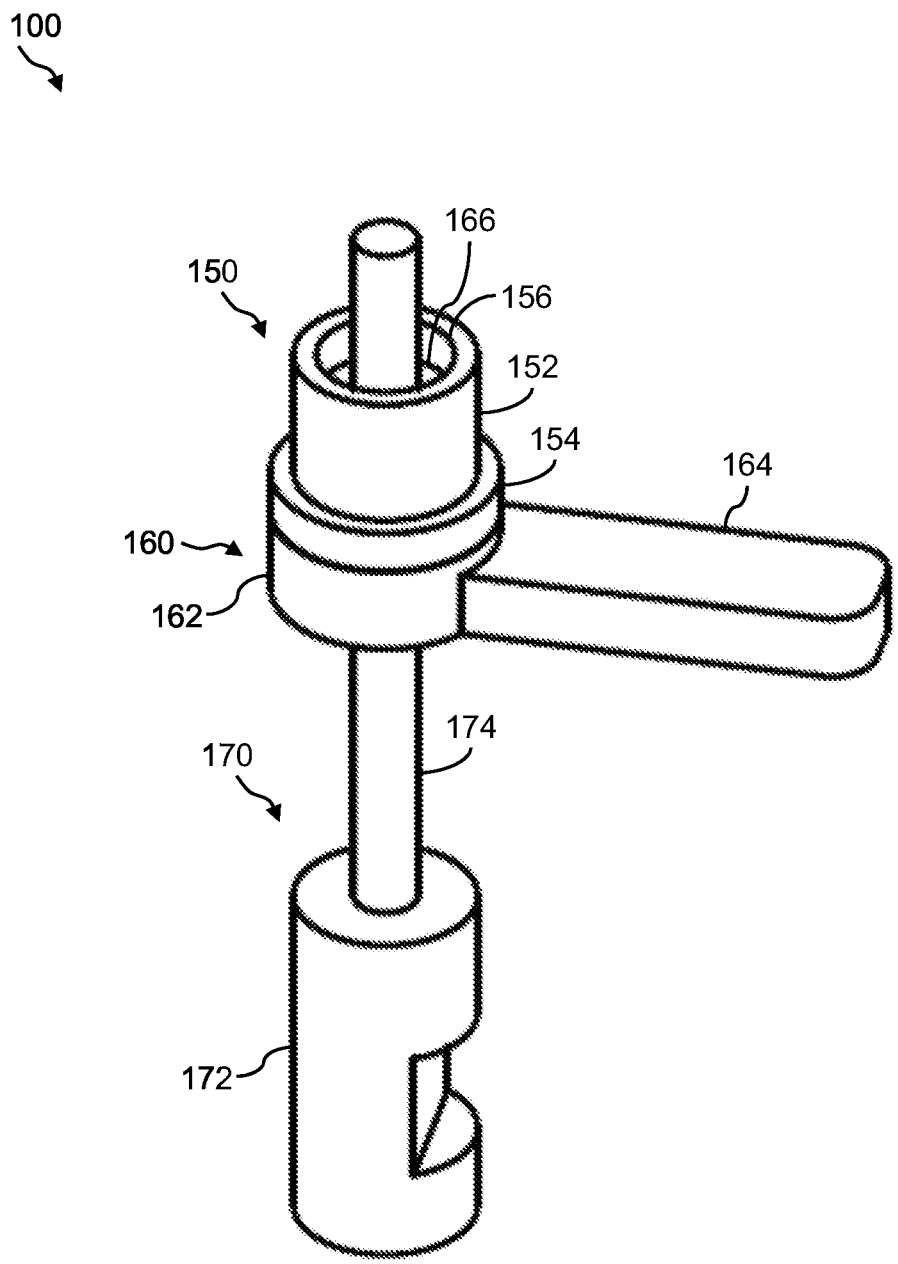
Figure 3:
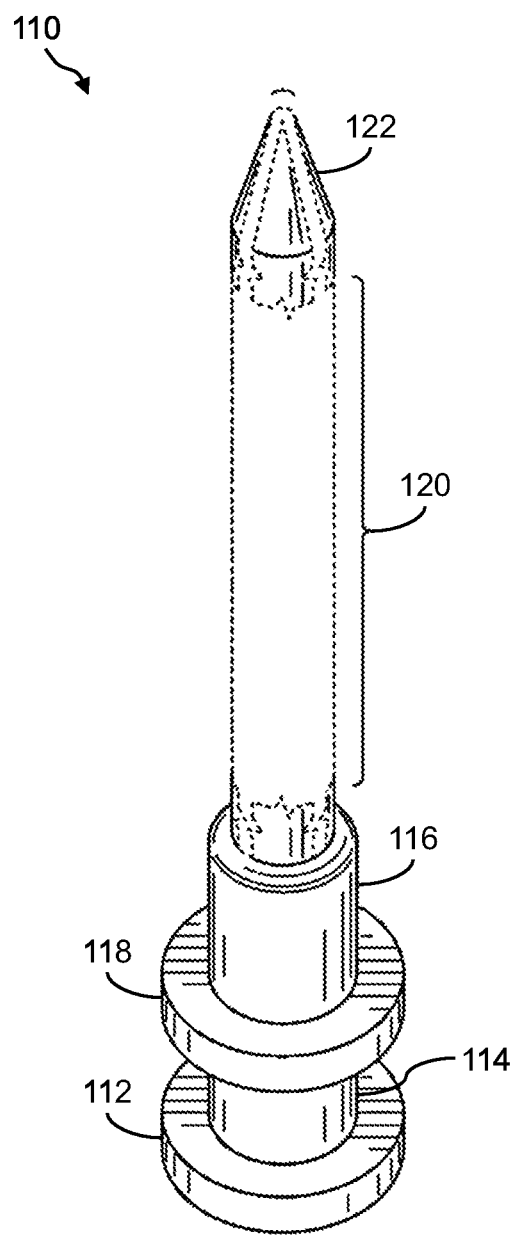
Figure 4A:
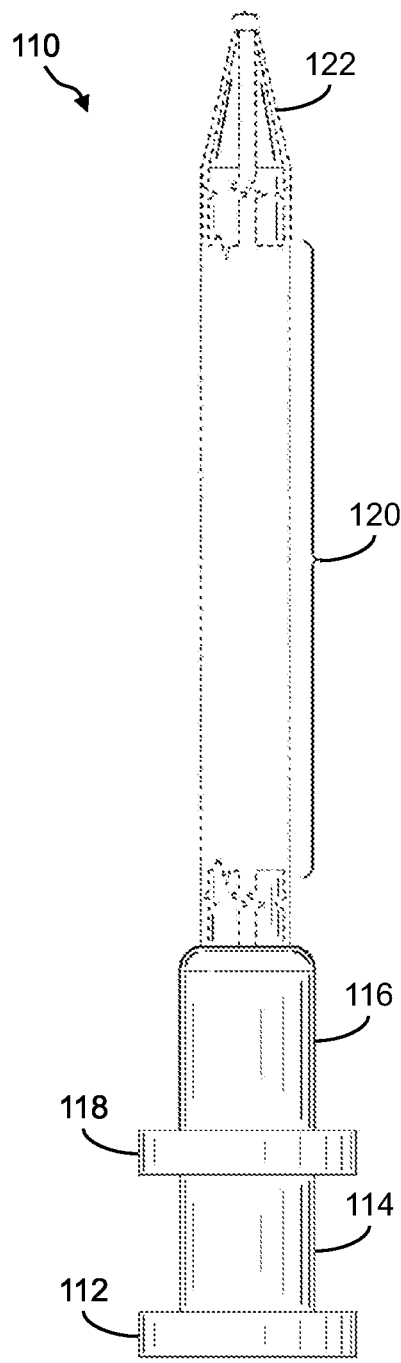
Figure 4B:
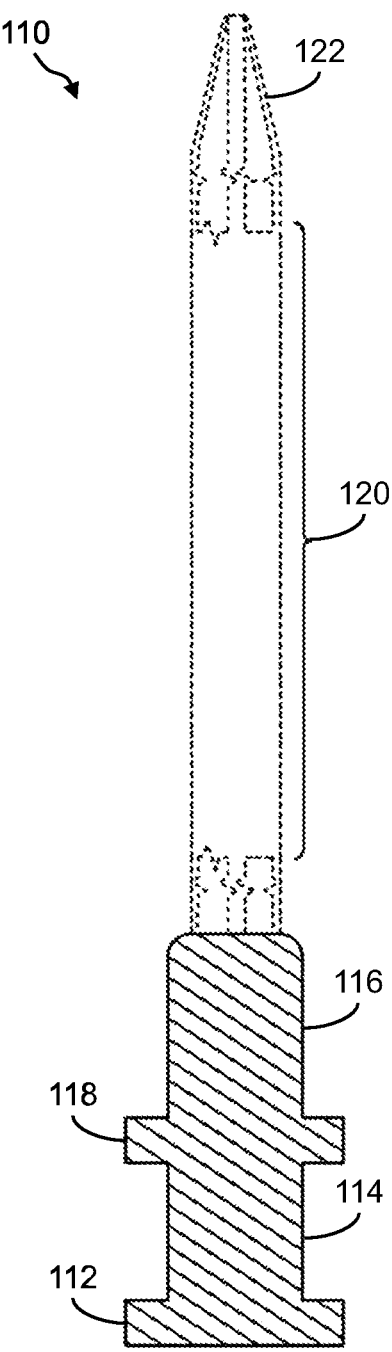
Figure 5A:
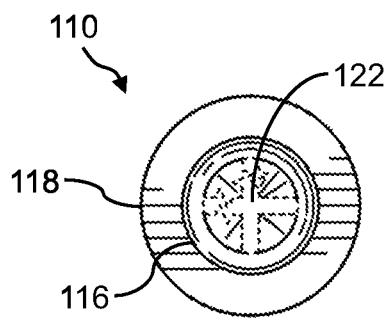
Figure 5B:
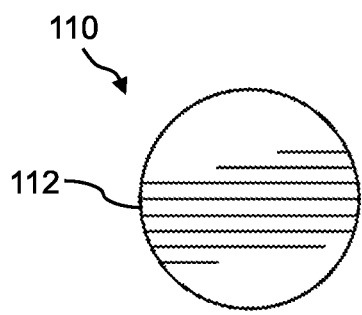
Figure 6:
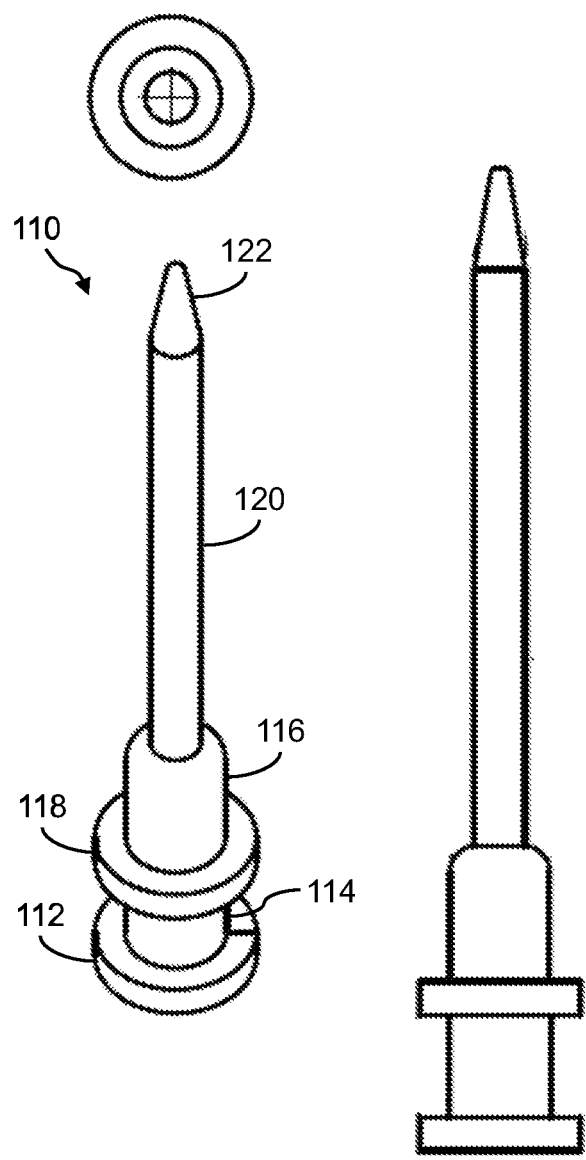
Figure 8:
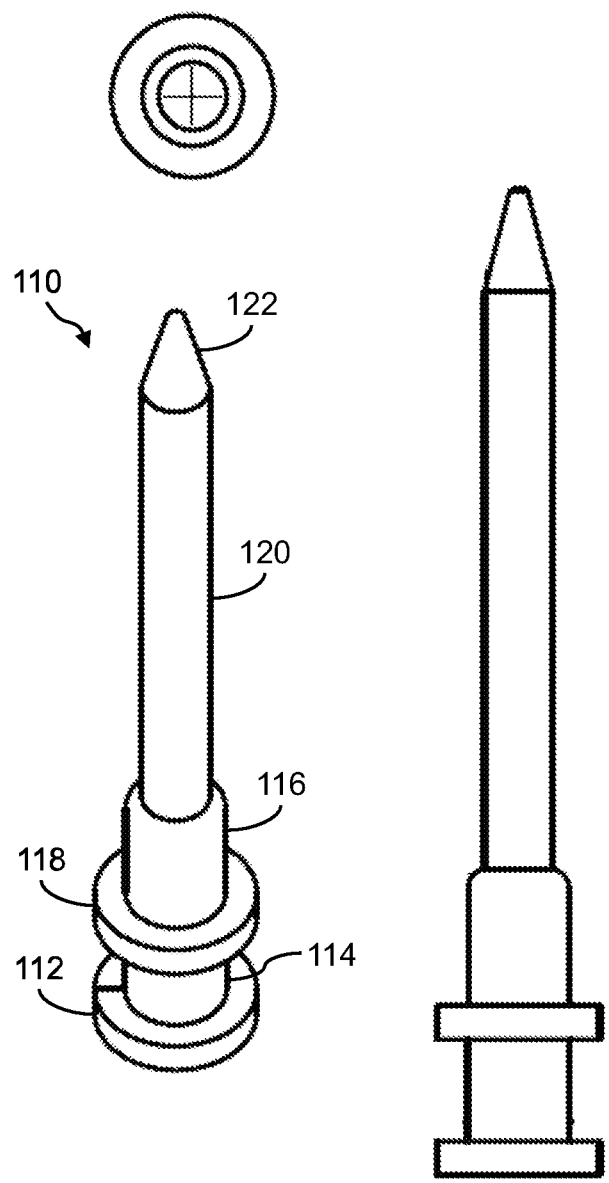
Figure 9:
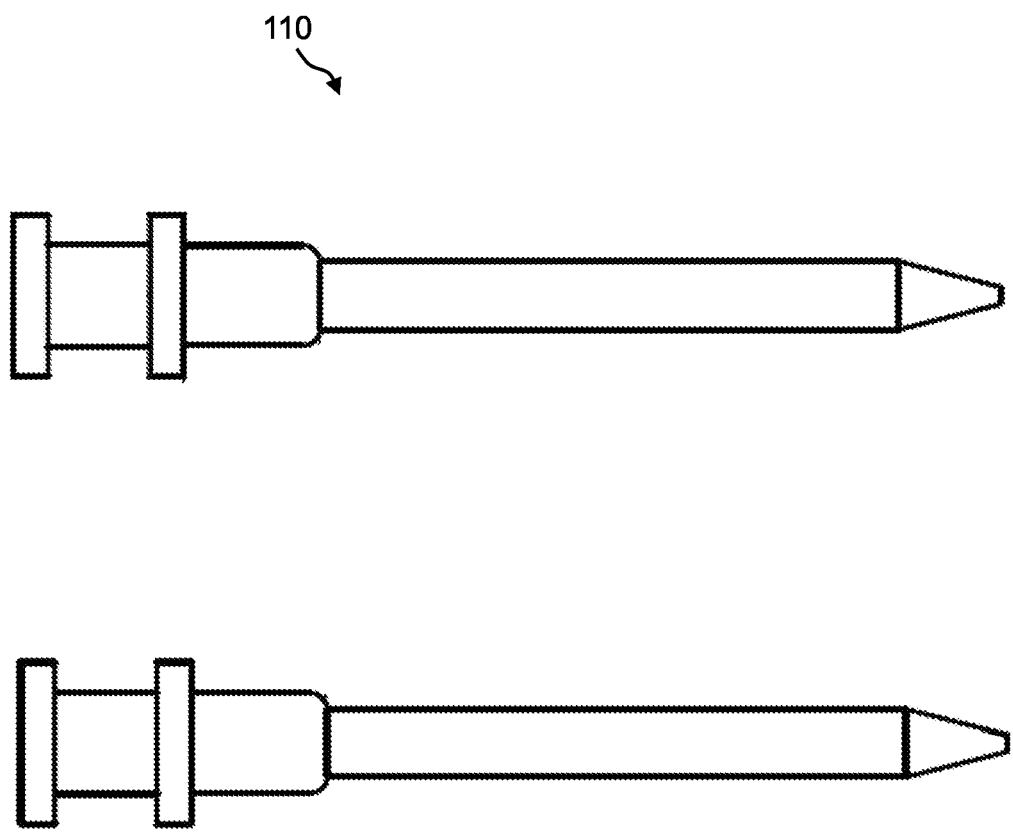
Figure 10:
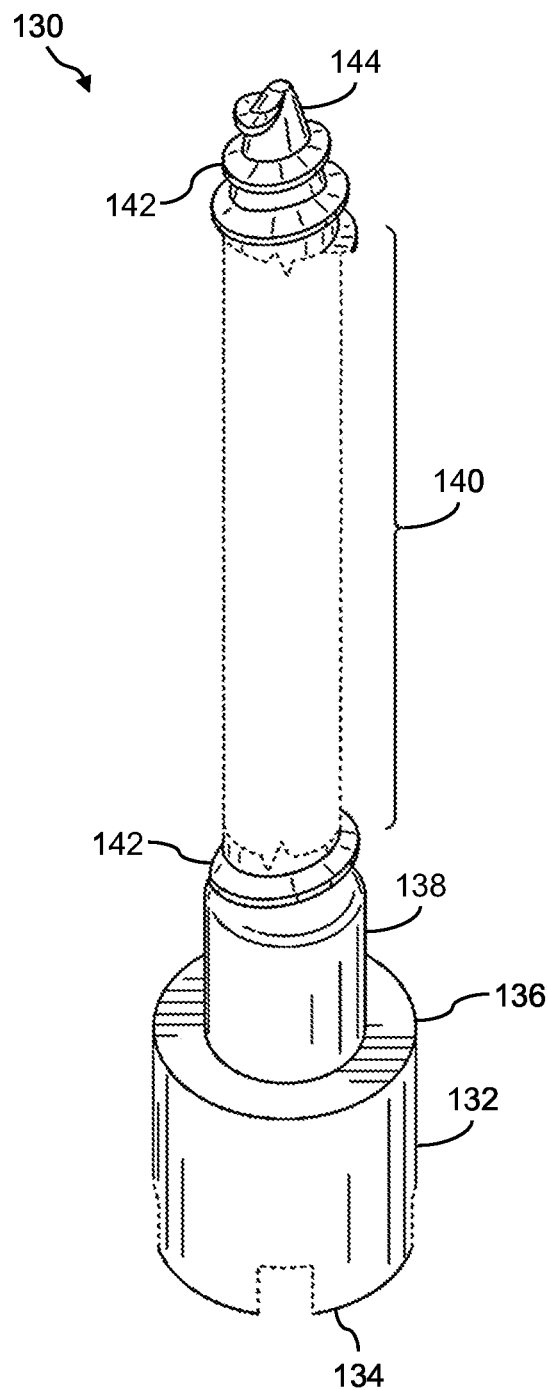
Figure 11A:
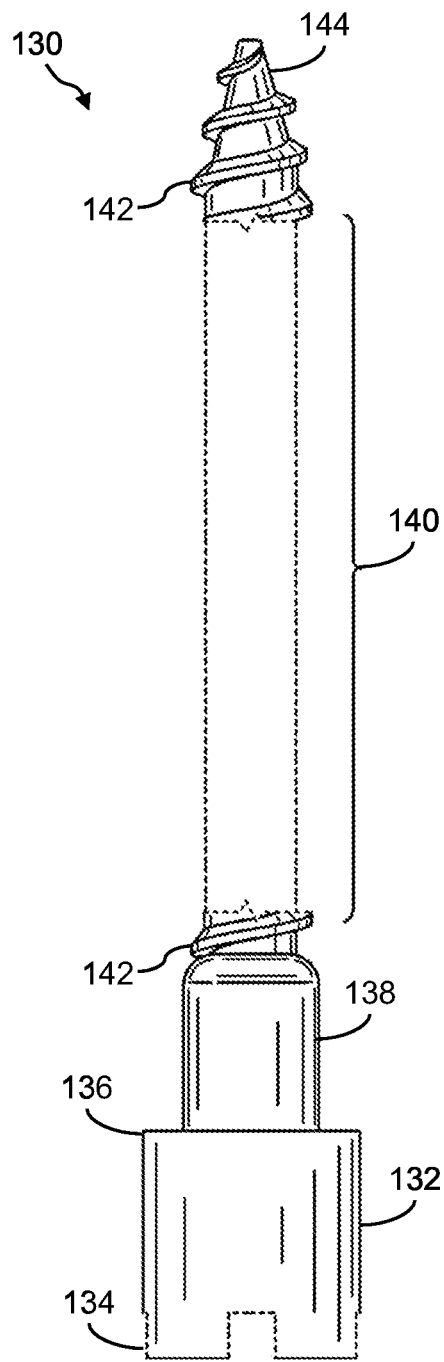
Figure 11B:
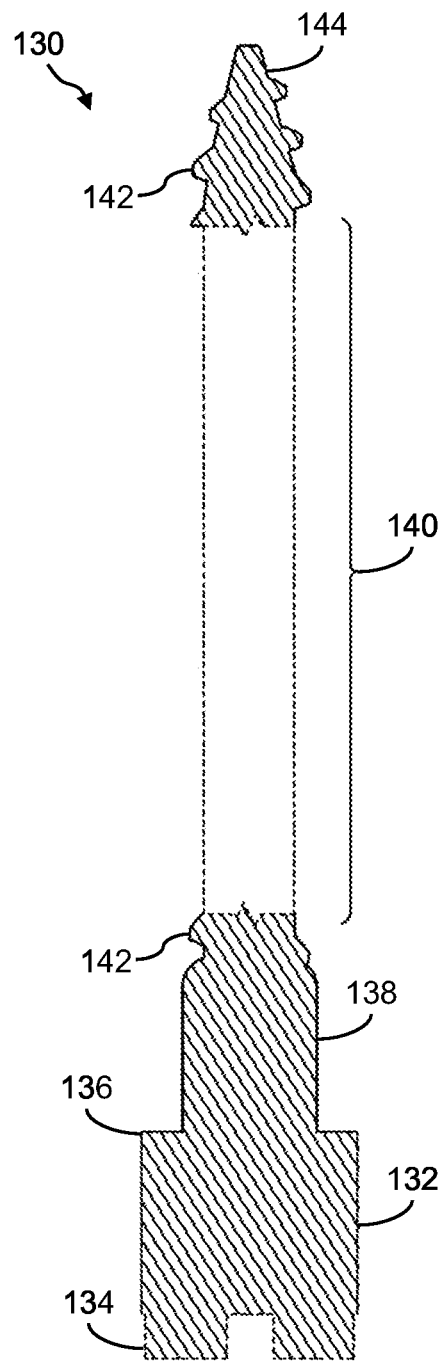
Figure 12A:
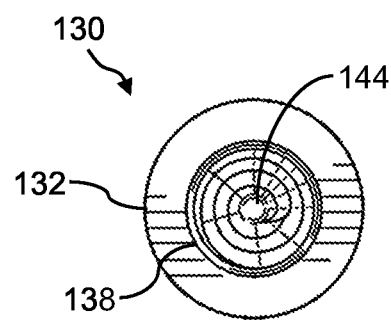
Figure 12B:
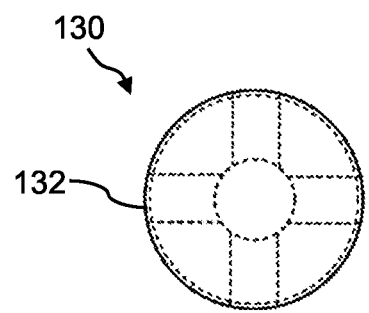
Figure 13:
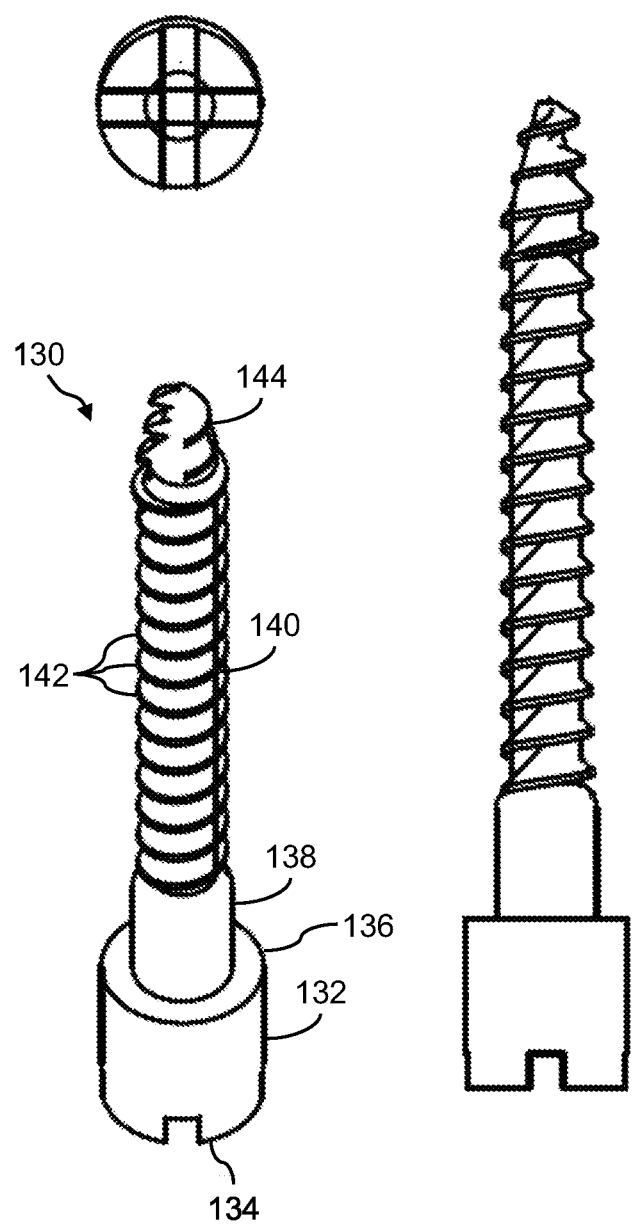
Figure 14:
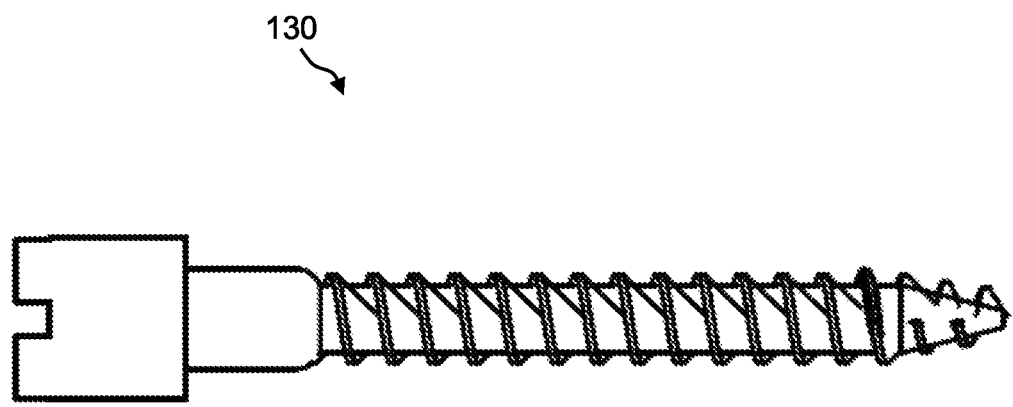
Figure 15A:
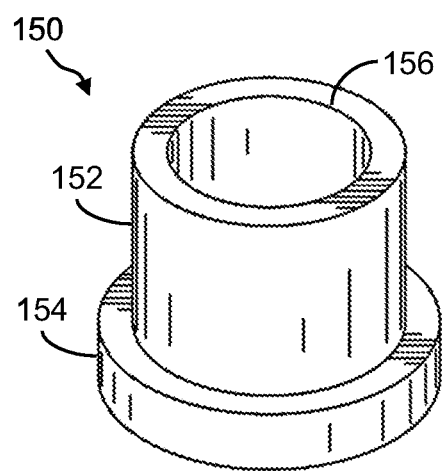
Figure 15B:
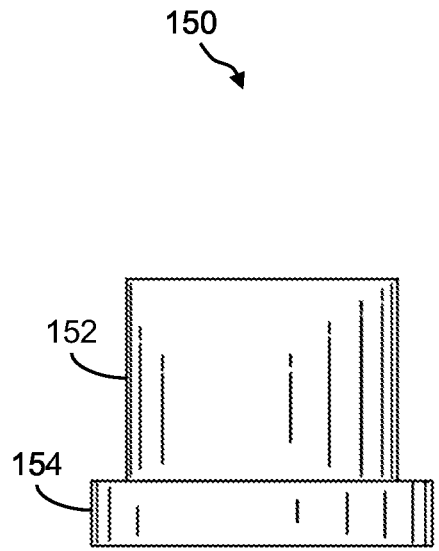
Figure 15C:
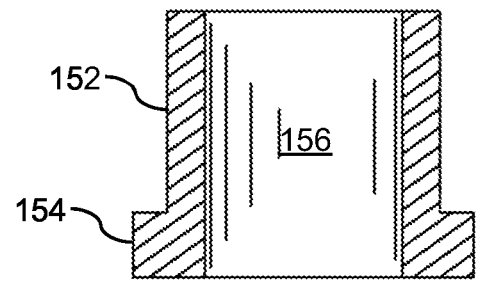
Figure 15D:
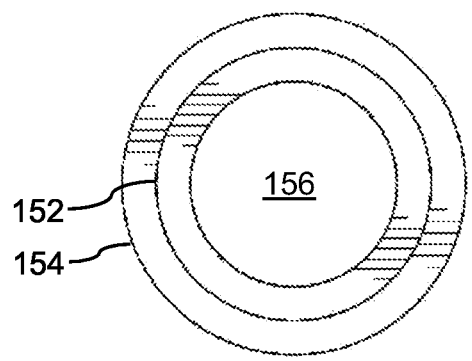
Figure 15E:
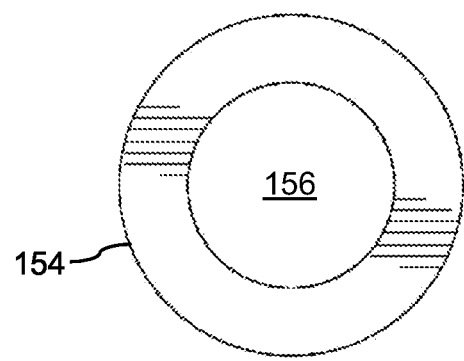
Figure 16:
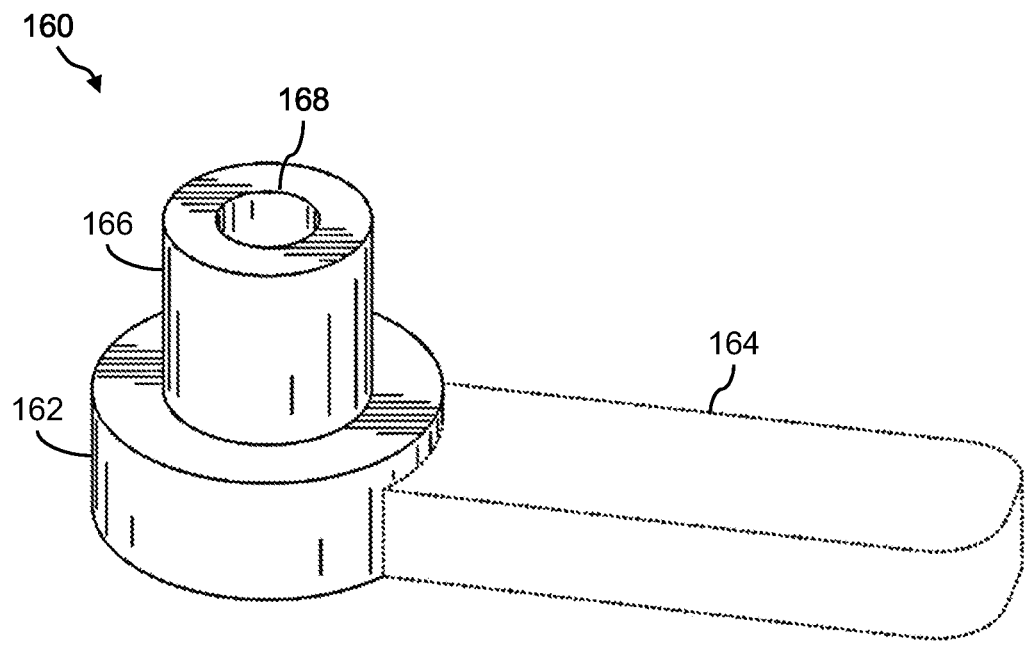
Figure 17A:
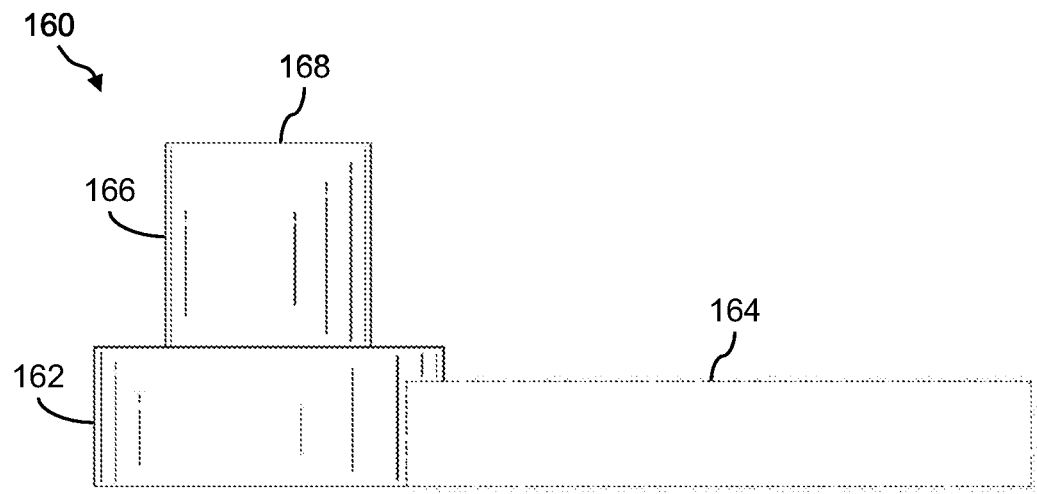
Figure 17B:
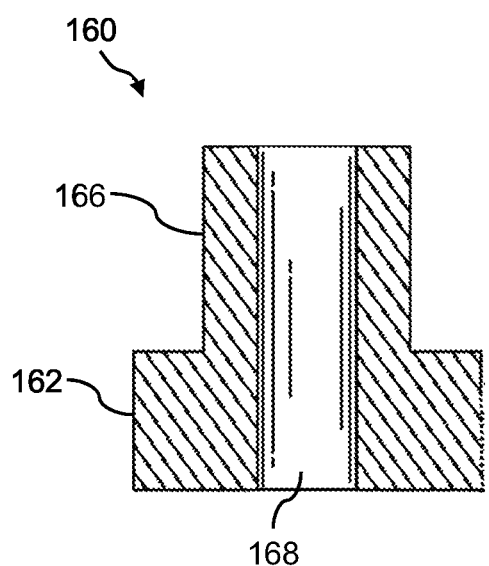
Figure 18A:
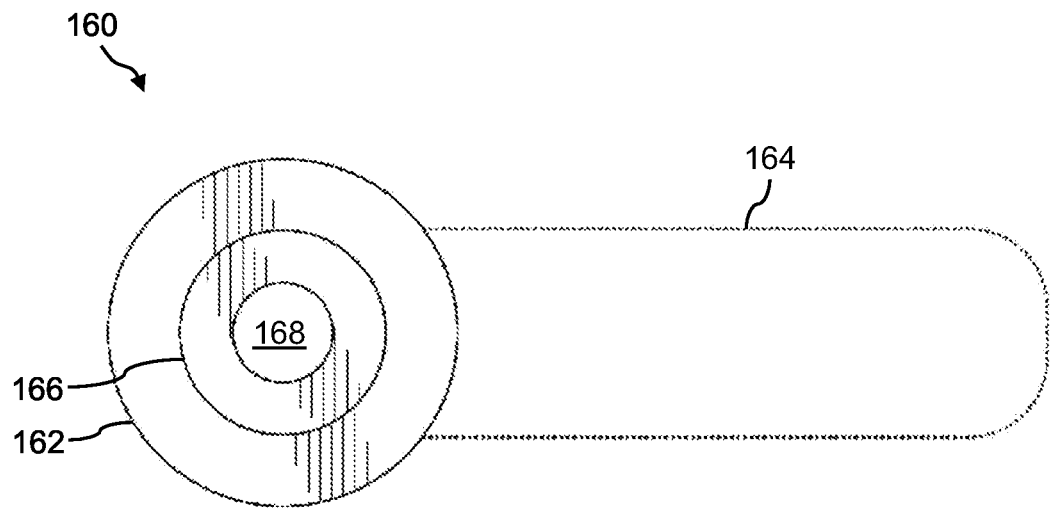
Figure 18B:
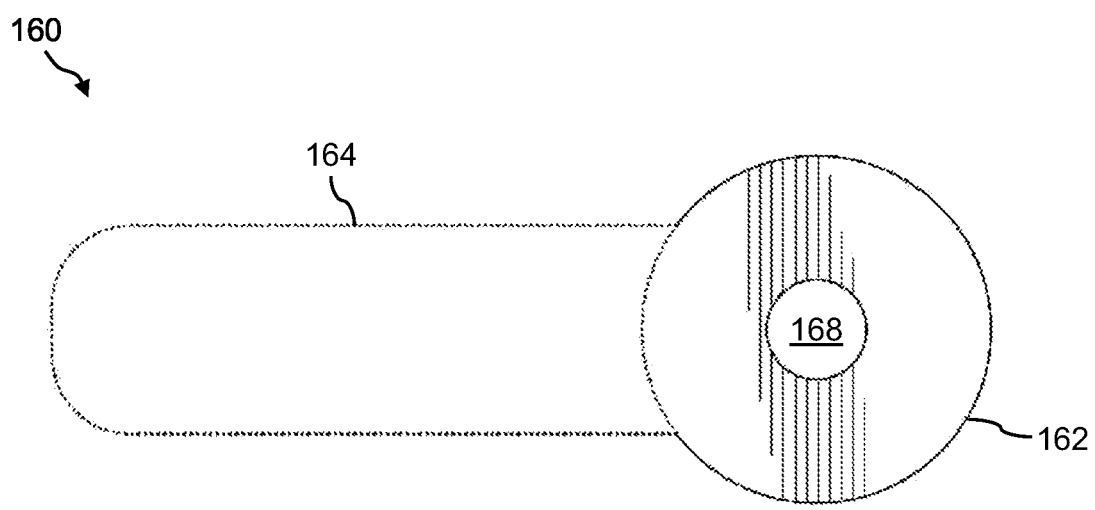
Figure 19:
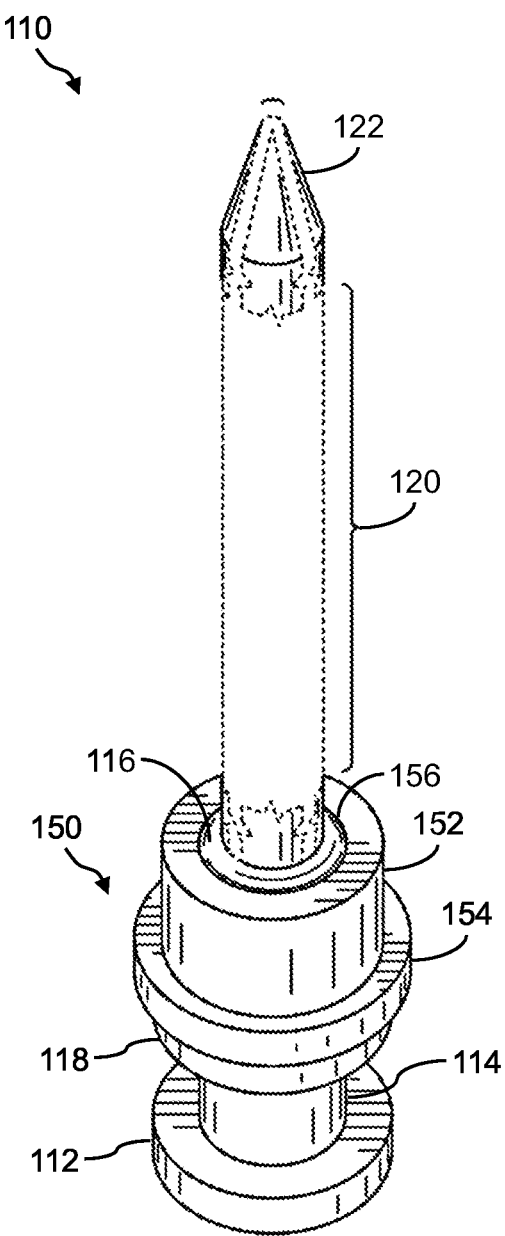
Figure 21:
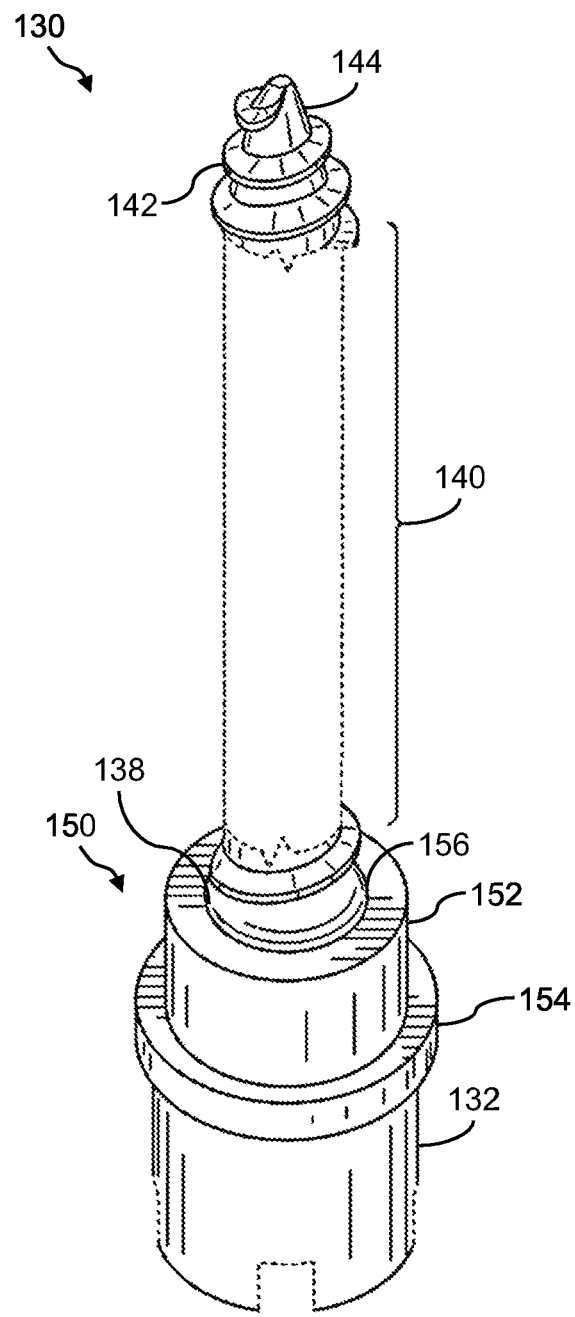
Figure 22A:
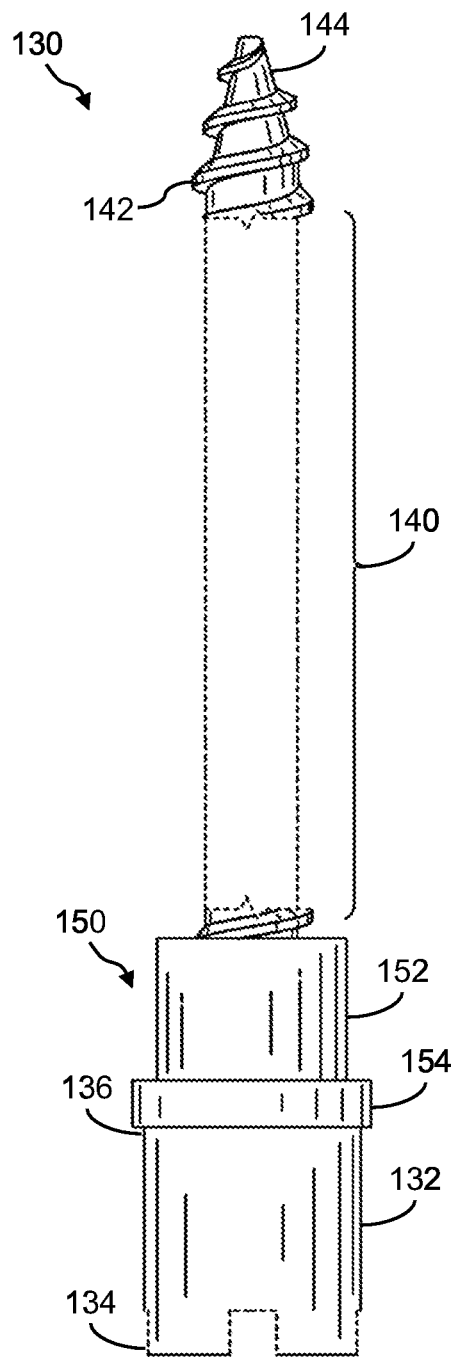
Figure 22B:
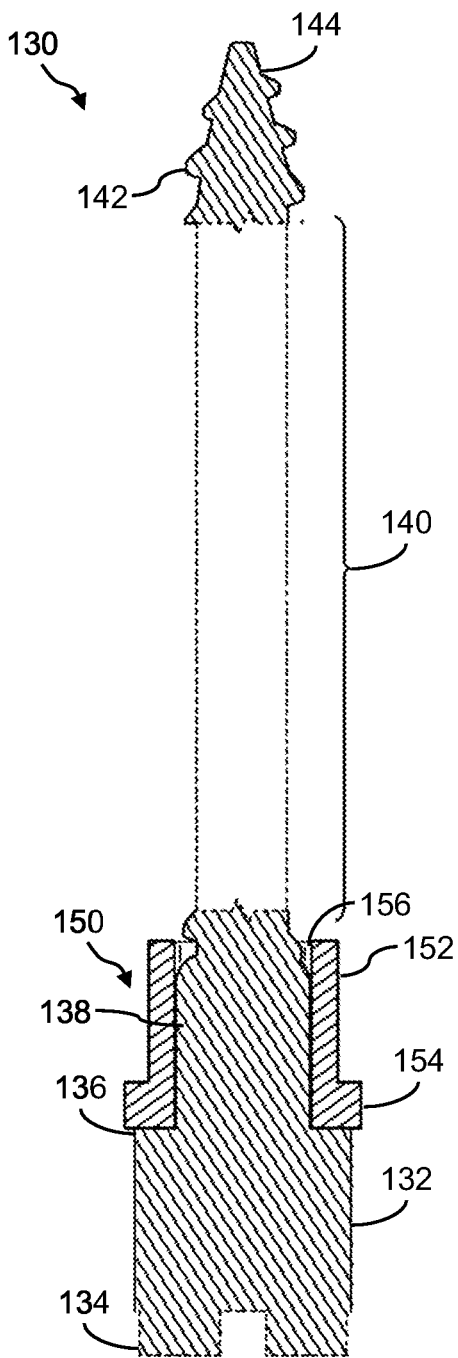
Figure 23:
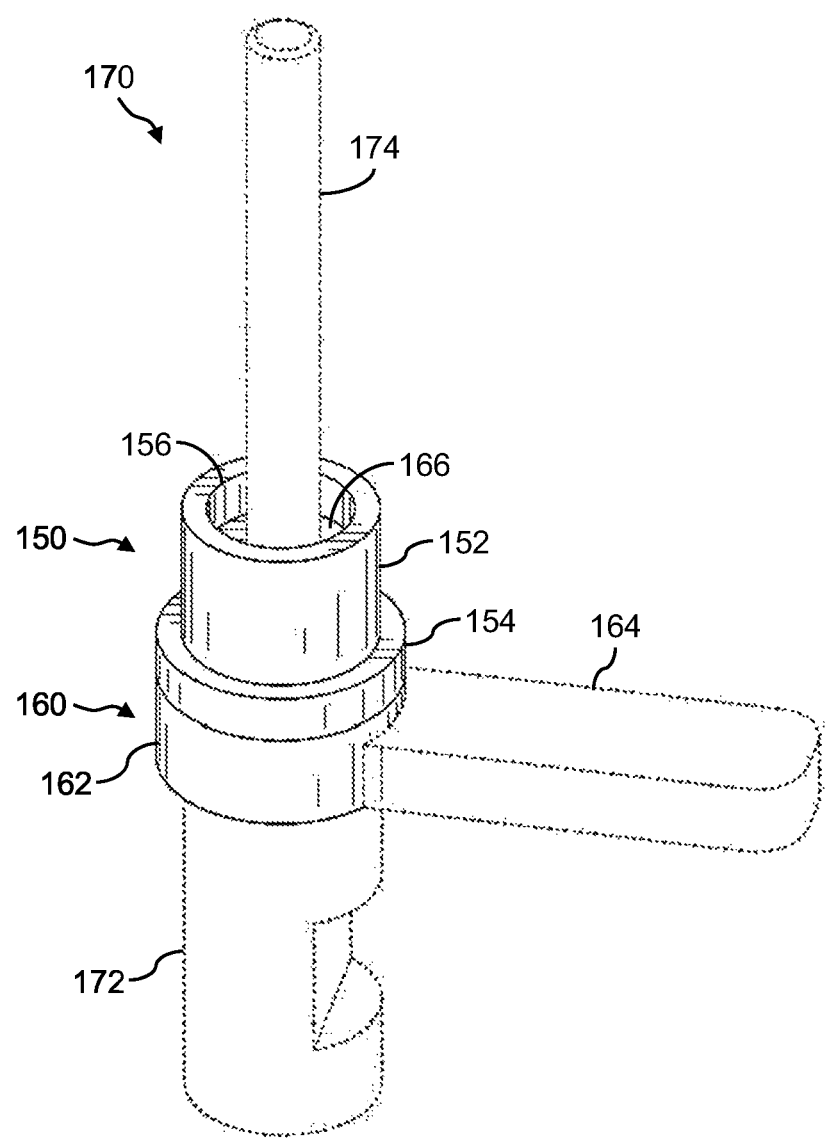
Figure 24:
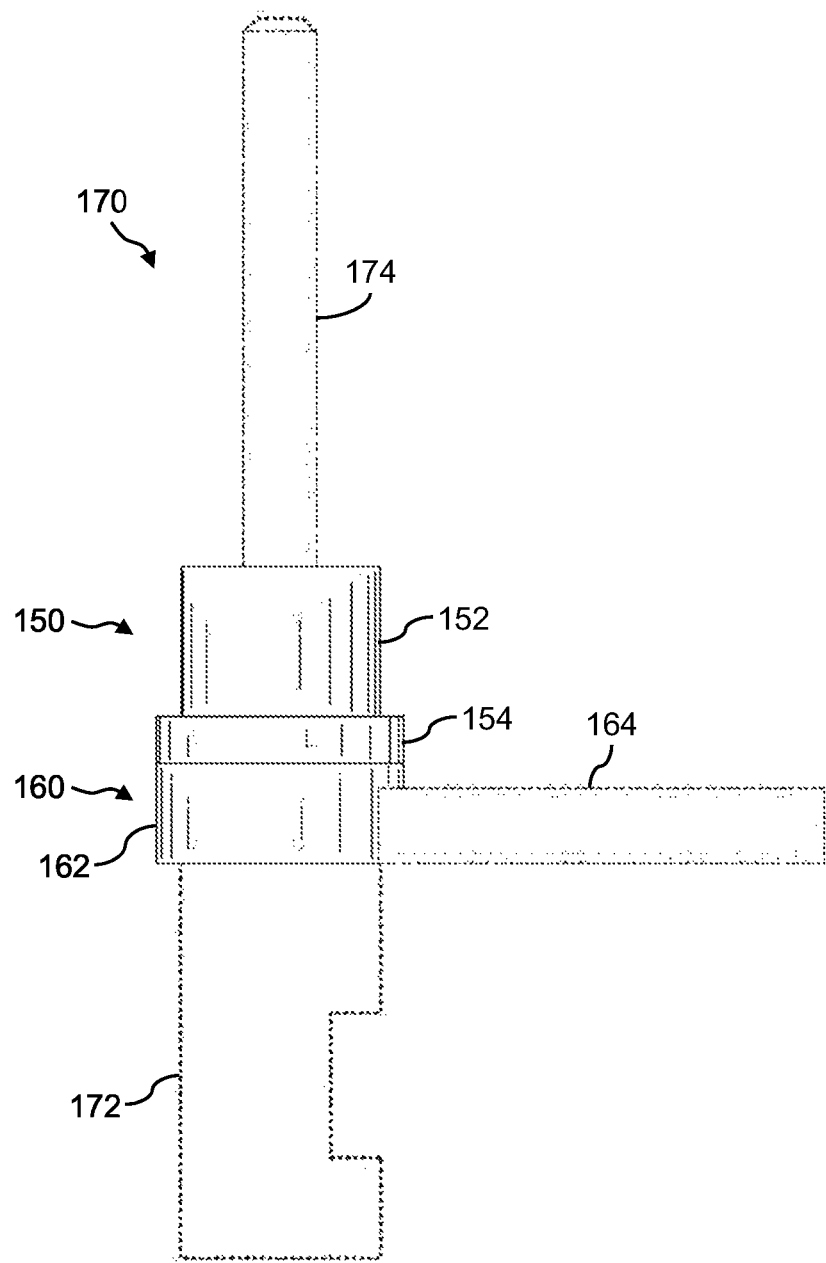
Figure 25:
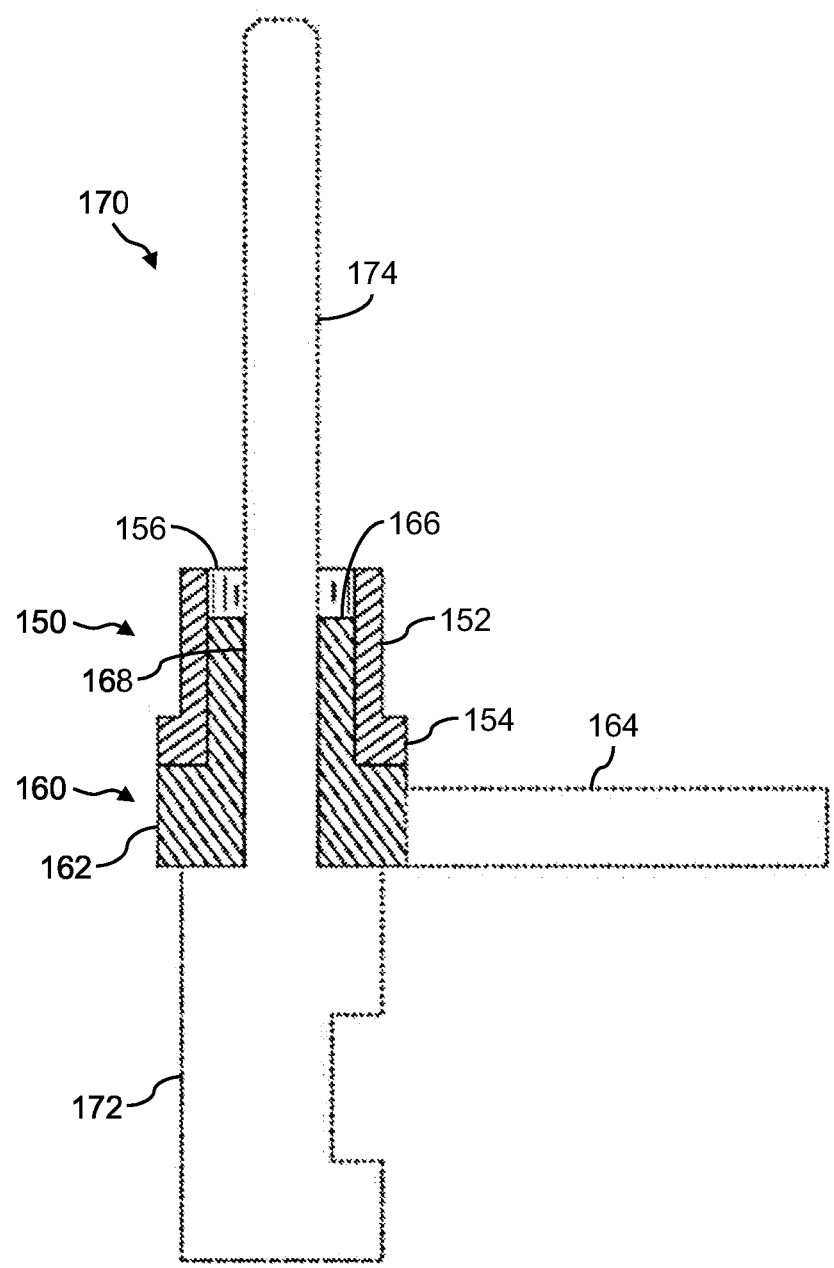
Figure 26:
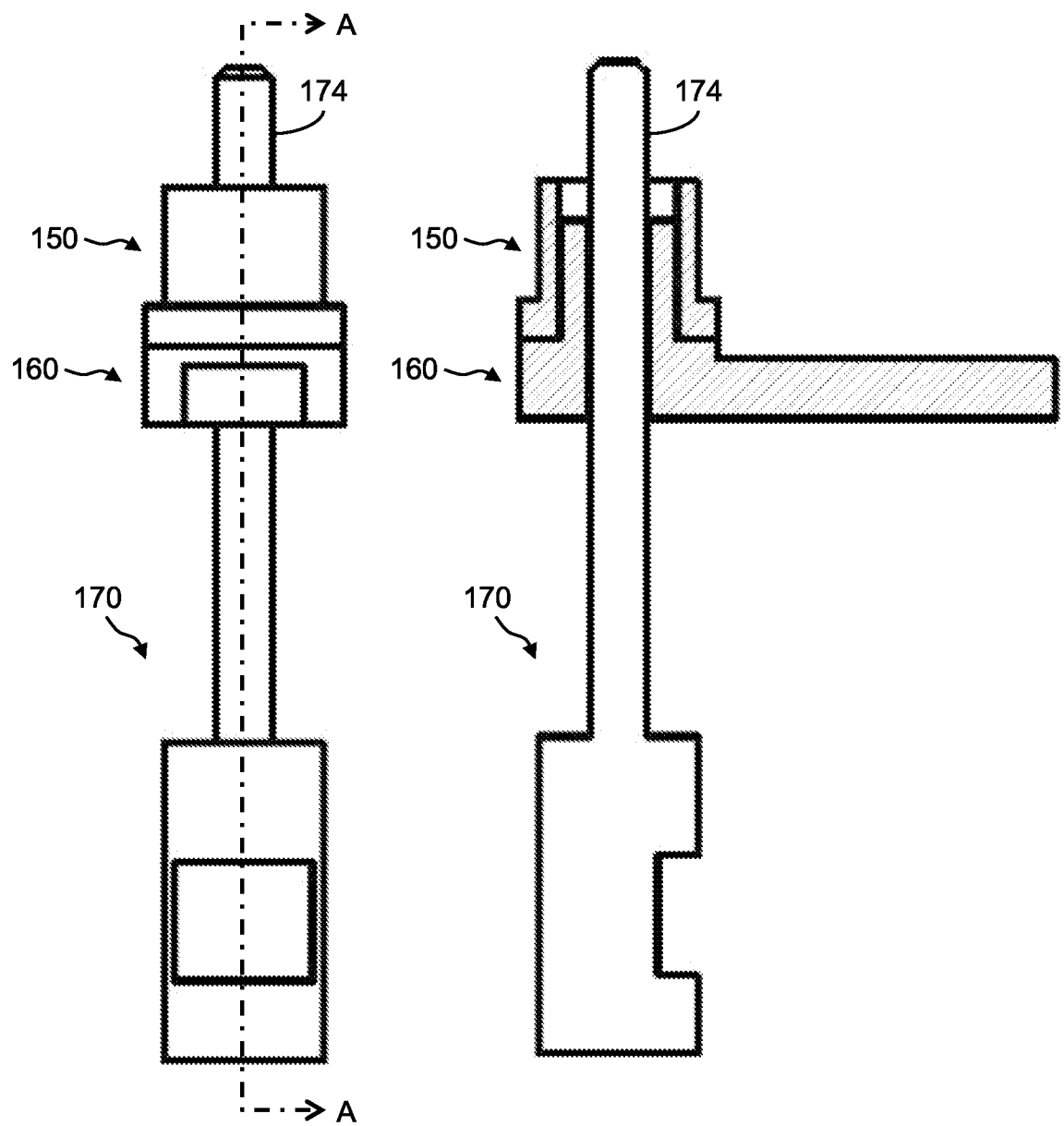
Figure 27:
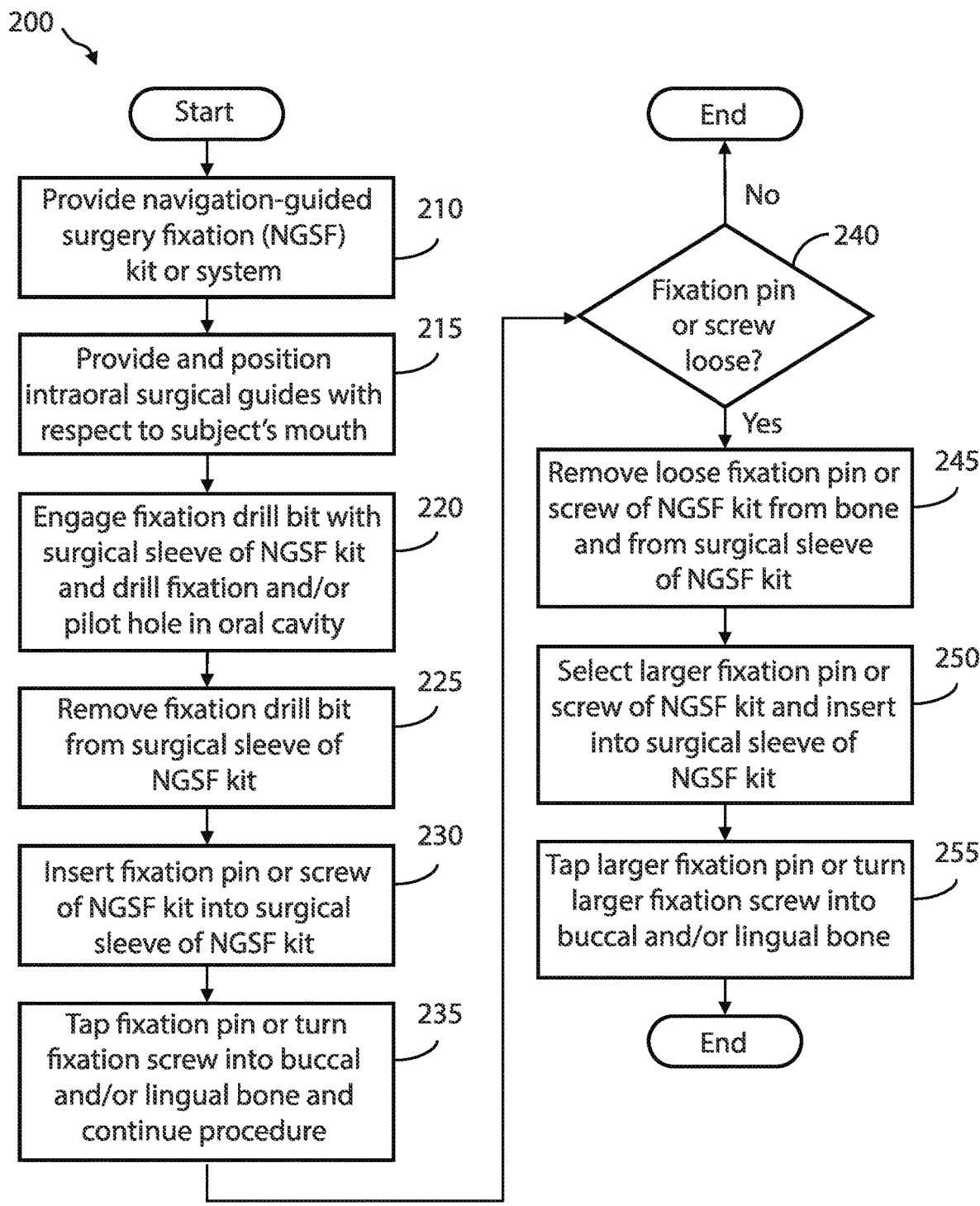

Having thus described the subject matter of the present invention in general terms, reference will now be made to the accompanying drawings, which are not necessarily drawn to scale, and wherein:

FIG. 1A, FIG. 1B, and FIG. 2 illustrate perspective views of an example of certain components of a NGSF kit (or system), in accordance with an embodiment of the invention;

FIG. 3, FIG. 4A, FIG. 4B, FIG. 5A, and FIG. 5B illustrate a perspective view, a side view, a cross-sectional view, a top view, and a bottom view, respectively, of an example of a fixation pin of the NGSF kit, in accordance with an embodiment of the invention;

FIG. 6 and FIG. 7 illustrate various views showing dimensions of an example of a fixation pin of the NGSF kit, in accordance with an embodiment of the invention;

FIG. 8 and FIG. 9 illustrate various views showing dimensions of another example of a fixation pin of the NGSF kit or system, in accordance with an embodiment of the invention;

FIG. 10, FIG. 11A, FIG. 11B, FIG. 12A, and FIG. 12B illustrate a perspective view, a side view, a cross-sectional view, a top view, and a bottom view, respectively, of an example of a fixation screw of the NGSF kit, in accordance with an embodiment of the invention;

FIG. 13 and FIG. 14 illustrate various views showing dimensions of an example of a fixation screw of the NGSF kit, in accordance with an embodiment of the invention;

FIG. 15A, FIG. 15B, FIG. 15C, FIG. 15D, and FIG. 15E illustrate a perspective view, a side view, a cross-sectional view, a top view, and a bottom view, respectively, of an example of a surgical sleeve of the NGSF kit, in accordance with an embodiment of the invention;

FIG. 16, FIG. 17A, FIG. 17B, FIG. 18A, and FIG. 18B illustrate a perspective view, a side view, a cross-sectional view, a top view, and a bottom view, respectively, of an example of a fixation drill key of the NGSF kit, in accordance with an embodiment of the invention;

FIG. 19, FIG. 20A, and FIG. 20B illustrate a perspective view, a side view, and a cross-sectional view, respectively, of an example of a fixation pin engaged with a surgical sleeve of the NGSF kit, in accordance with an embodiment of the invention;

FIG. 21, FIG. 22A, and FIG. 22B illustrate a perspective view, a side view, and a cross-sectional view, respectively, of an example of a fixation screw engaged with a surgical sleeve of the NGSF kit, in accordance with an embodiment of the invention;

FIG. 23, FIG. 24, and FIG. 25 illustrate a perspective view, a side view, and a cross-sectional view, respectively, of an example of the surgical sleeve, the fixation drill key, and a fixation drill bit of the NGSF kit assembled together, in accordance with an embodiment of the invention;

FIG. 26 illustrates another side view and cross-sectional view of an example of the surgical sleeve, the fixation drill key, and the fixation drill bit of the NGSF kit assembled together, in accordance with an embodiment of the invention; and FIG. 27 illustrates a flow diagram of an example of a method of using the navigation-guided surgery fixation kit, in accordance with an embodiment of the invention.

DETAILED DESCRIPTION

The subject matter of the present invention now will be described more fully hereinafter with reference to the accompanying drawings, in which some, but not all embodiments of the subject matter of the present invention are shown. Like numbers refer to like elements throughout. The subject matter of the present invention may be embodied in many different forms and should not be construed as limited to the embodiments set forth herein; rather, these embodiments are provided so that this disclosure will satisfy applicable legal requirements. Indeed, many modifications and other embodiments of the subject matter of the present invention set forth herein will come to mind to one skilled in the art to which the subject matter of the present invention pertains having the benefit of the teachings presented in the foregoing descriptions and the associated drawings. Therefore, it is to be understood that the subject matter of the present invention is not to be limited to the specific embodiments disclosed and that modifications and other embodiments are intended to be included within the scope of the appended claims.

In some embodiments, the subject matter of the present invention provides a navigation-guided surgery fixation (NGSF) kit or system and method of using same.

In some embodiments, the NGSF kit or system and method provide mechanisms suitable for use in intraoral guided surgery procedures, such as, but not limited to, bone fixated (bone touching/contacting) guide-assisted surgical procedures.

In some embodiments, the NGSF kit or system and method may provide a fixation pin and/or a fixation screw, a surgical sleeve, and a fixation drill bit including a fixation drill key.

In some embodiments, the NGSF kit or system and method may provide a fixation pin that may include a pin head, a pin shank, a pin shaft, and a pin tip and wherein the pin shank has a certain diameter and the pin shaft has a certain diameter that is smaller than the pin shank diameter and wherein the surgical sleeve hole diameter is sized to the nominal diameter of the pin shank, instead of to the nominal diameter of the pin shaft.

In some embodiments, the NGSF kit or system and method may provide a fixation screw that may include a screw head, a screw shank, a threaded screw shaft, and a screw tip and wherein the screw shank has a certain diameter and the screw shaft has a certain diameter that is smaller than the screw shank diameter and wherein the surgical sleeve hole diameter is sized to the nominal diameter of the screw shank, instead of to the nominal diameter of the screw shaft.

In some embodiments, the NGSF kit or system and method may provide a surgical sleeve that may include a cylindrical sleeve body with a sleeve baseplate on one end and a through-hole through the entirety of the surgical sleeve and wherein the diameter of the cylindrical sleeve body may be sized to fit in the fixation guide hole of a surgical guide and wherein the through-hole diameter of the surgical sleeve may be sized to receive the pin shank of the fixation pin and/or the screw shank of the fixation screw.

In some embodiments, the NGSF kit or system and method may provide fixation pins and/or fixation screws with an incremented pin shaft and/or screw shaft diameter. For example, a first fixation pin having a pin shaft diameter of about 1.5 mm and a pin shank diameter of about 2.94 mm and a second fixation pin having a pin shaft diameter of about 2 mm and a pin shank diameter of about 2.94 mm. In this example, the first and second fixation pins have different pin shaft diameters but the same pin shank diameters.

In some embodiments, the NGSF kit or system and method may provide a fixation drill bit for fitting through a fixation drill key that may be fitted into the aforementioned surgical guide that may be fitted in the fixation guide hole of a surgical guide and used to drill a fixation and/or pilot hole in the oral cavity of a subject during an intraoral guided surgery procedure.

Further, a method of using the NGSF kit or system is provided.

Referring now to FIG. 1A, FIG. 1B, and FIG. 2 is perspective views of an example of certain components of a NGSF kit (or system) 100, in accordance with an embodiment of the invention. NGSF kit 100 may include, for example, one or more of a fixation pin 110 (see FIG. 1A) and/or a fixation screw 130 (see FIG. 1B), a surgical sleeve 150 (see FIG. 1A. FIG. 1B, and FIG. 2), a fixation drill key 160 (see FIG. 2), and/or a fixation drill bit 170 (see FIG. 2). Fixation pin 110, fixation screw 130, surgical sleeve 150, fixation drill key 160, and fixation drill bit 170 may be formed, for example of 316L stainless steel or any other suitable material used in intraoral guided surgery procedures. For example, fixation pin 110 may be a solid stainless steel pin. Likewise, fixation screw 130 may be a solid stainless steel screw.

In one example and referring now to FIG. 1A, fixation pin 110 may include a pin head 112 with a spacer 114, a pin shank 116 with a baseplate 118, and a pin shaft 120 with a pin tip 122. Pin head 112 of fixation pin 110 may be shaped to be easily manipulated by surgical tools, such as hemostats. More details of examples of fixation pin 110 are shown and described hereinbelow with reference to FIG. 3 through FIG. 9.

In one example and referring now to FIG. 1B, fixation screw 130 may include a fixation screw head 132 with a slot end 134 and a screw end 136, a screw shank 138, a screw shaft 140 with threads 142 (e.g., British Standard buttress threads), and a self-tapping screw tip 144 at the end of screw shaft 140. Fixation screw head 132 with slot end 134 of fixation screw 130 may be shaped to accept common surgical drivers. More details of examples of fixation screw 130 are shown and described hereinbelow with reference to FIG. 10 through FIG. 14.

In one example and referring now to FIG. 1A. FIG. 1B, and FIG. 2, surgical sleeve 150 may include a sleeve body 152 with a sleeve baseplate 154, and a through-hole 156 passing through the entirety of sleeve body 152 and sleeve baseplate 154. More details of examples of surgical sleeve 150 are shown and described hereinbelow with reference to FIG. 15A through FIG. 15E.

In one example and referring now to FIG. 2, fixation drill key 160 may include a drill key body 162, a drill key arm 164, a drill key shank 166, and a through-hole 168 (not visible) passing through the entirety of drill key body 162 and drill key shank 166. More details of examples of fixation drill key 160 are shown and described hereinbelow with reference to FIG. 17 through FIG. 18B.

In one example and referring now to FIG. 2, fixation drill bit 170 may include a drill bit shank 172 and a drill bit 174. Fixation drill bit 170 may be any drill suitable for the piloting and placement of fixation pins and screws in the oral cavity. Optionally, a trephine burr, end mill, profile drill, or other suitable drill bit may be used to normalize the surface of the bone at the fixation site. Fixation drill bit 170 may be guided by surgical sleeve 150 and/or fixation drill key 160. More details of examples of fixation drill bit 170 are shown and described hereinbelow with reference to FIG. 23 through FIG. 26.

Fixation pin 110, fixation screw 130, surgical sleeve 150, fixation drill key 160, and fixation drill bit 170 of NGSF kit 100 are mechanisms that may be suitable for use with surgical guides (not shown) that may be used in intraoral guided surgery procedures, such as, but not limited to, bone fixated (bone touching/contacting) guide-assisted surgical procedures.

In NGSF kit 100, sleeve body 152 of surgical sleeve 150 may be designed to be fitted into the fixation guide hole of a surgical guide. Then, the pin shank 116—portion of fixation pin 110 may be designed to be fitted into through-hole 156 of surgical sleeve 150. An example of fixation pin 110 fitted together with surgical sleeve 150 is shown and described hereinbelow with reference to FIG. 19, FIG. 20A, and FIG. 20B.

Likewise, the screw shank 138—portion of fixation screw 130 may be designed to be fitted into through-hole 156 of surgical sleeve 150. An example of fixation screw 130 fitted together with surgical sleeve 150 is shown and described hereinbelow with reference to FIG. 21, FIG. 22A, and FIG. 22B.

Additionally, during the drilling process of an intraoral guided surgery procedure, fixation drill key 160 and drill bit 174 of fixation drill bit 170 may be installed into surgical sleeve 150 (see FIG. 2). Then, sleeve body 152 of surgical sleeve 150 fitted into the fixation guide hole of a surgical guide (not shown) to guide drill bit 174 in the drilling process. An example of surgical sleeve 150, fixation drill key 160, and fixation drill bit 170 fitted together is shown and described hereinbelow with reference to FIG. 23 through FIG. 26.

Currently, the diameter of conventional fixation pins is limited to the diameter of the surgical sleeve (the open shaft the pin slides through). Commonly, the surgical sleeve inner diameter will be the nominal dimension of the pin. Therefore, once a pin loosens within the bone, it is impossible to insert a larger pin due to the diameter restriction of the surgical sleeve. Referring now again to FIG. 1A, FIG. 1B, and FIG. 2, a main benefit of NGSF kit 100 is that it may be used to overcome the problem. For example, NGSF kit 100 may allow the loose fixation pin or screw to be removed and replaced with a larger fixation pin or screw.

More specifically, in NGSF kit 100, a common sized shank may be added to the fixation pin or screw that has a larger diameter than the pin or screw shaft itself. Then, the surgical sleeve is sized to the nominal diameter of the shank, instead of the nominal diameter of the pin. For example, fixation pin 110 may include pin shank 116 that has a larger diameter than the pin shaft 120 itself. Likewise, fixation screw 130 may include screw shank 138 that has a larger diameter than the screw shaft 140 itself. Then, through-hole 156 of surgical sleeve 150 may be sized to the nominal diameter of pin shank 116 and/or screw shank 138, instead of to the nominal diameter of pin shaft 120 and/or screw shaft 140.

By designing fixation pins 110 and/or fixation screws 130 of NGSF kit 100 to share a common shank diameter for the single corresponding sleeve diameter, the fixations in NGSF kit 100 may be interchangeable. Each fixation pin 110 and/or fixation screw 130 may be designed with an incremented pin shaft and/or screw shaft diameter. For example, the 1.5 mm-shaft of the fixation pin 110 shown in FIG. 6 and FIG. 7 and the 2.0 mm-shaft of the fixation pin 110 shown in FIG. 8 and FIG. 9, but both with the same pin shank 116 diameter. Therefore, during a surgery, a fixation pin 110 presently inserted may be removed and replaced with one which has a larger pin shaft diameter but having the same pin shank 116 diameter. This allows a surgeon to regain stability of a guide that has been lost as fixation loosens.

With respect to the hole diameter reducer function of surgical sleeve 150, the intraoral guided surgery procedure may begin with one or more surgical sleeves 150 installed in the fixation guide holes of a surgical guide (not shown) and wherein the through-holes 156 of surgical sleeves 150 may have a certain diameter. Next, at each surgical sleeve 150, fixation pin 110 or fixation screw 130 may be fitted into through-hole 156 of surgical sleeve 150 and then secured (tapped in or screwed) into the bone of the subject. In the installation process of fixation pin 110, the pin shank 116—portion of fixation pin 110 seats into through-hole 156 of surgical sleeve 150 while the smaller diameter pin shaft 120—portion of fixation pin 110 engages the bone. Likewise, in the installation process of fixation screw 130, the screw shank 138—portion of fixation screw 130 seats into through-hole 156 of surgical sleeve 150 while the smaller diameter screw shaft 140—portion of fixation screw 130 engages the bone.

However, if at any time during the intraoral guided surgery procedure any fixation pin 110 or fixation screw 130 loosens, then NGSF kit 100 provides the remedy. For example, at any position in which the fixation pin 110 or fixation screw 130 is loose, the surgeon may remove the loose fixation pin 110 or fixation screw 130. Then, the surgeon may install a larger diameter fixation pin or screw in the original and larger diameter fixation guide hole to resecure the surgical guide. For example, the surgeon may have removed the loosened 1.5 mm-shaft fixation pin 110 (see FIG. 6 and FIG. 7) and may now install the 2.0 mm-shaft fixation pin 110 (see FIG. 8 and FIG. 9), but both with the same pin shank 116 diameter to be fitted into surgical sleeve 150.

Referring now to FIG. 3, FIG. 4A, FIG. 4B, FIG. 5A, and FIG. 5B is a perspective view, a side view, a cross-sectional view, a top view, and a bottom view, respectively, of an example of fixation pin 110 of NGSF kit 100, in accordance with an embodiment of the invention.

Additionally, FIG. 6 and FIG. 7 show various views showing dimensions (in mm) of an example of fixation pin 110 of NGSF kit 100. In this example, the overall length of fixation pin 110 may be about 29 mm, the diameter of spacer 114 may be about 3 mm, the diameter of pin shank 116 may be about 2.94 mm, the diameter of pin shaft 120 may be about 1.5 mm, and the length of pin shaft 120 including pin tip 122 may be about 20 mm. Accordingly, in this example, the diameter of through-hole 156 of surgical sleeve 150 that is designed to receive the pin shank 116—portion of fixation pin 110 may be about 3.0 mm.

Additionally, FIG. 8 and FIG. 9 show various views showing dimensions (in mm) of another example of fixation pin 110 of NGSF kit 100. In this example, the overall length of fixation pin 110 may be about 29 mm, the diameter of spacer 114 may be about 3 mm, the diameter of pin shank 116 may be about 2.94 mm, the diameter of pin shaft 120 may be about 2 mm, and the length of pin shaft 120 including pin tip 122 may be about 20 mm. Again, in this example, the diameter of through-hole 156 of surgical sleeve 150 that is designed to receive the pin shank 116—portion of fixation pin 110 may be about 3.0 mm. In fixation pin 110 of FIG. 6 and FIG. 7, the diameter of pin shaft 120 may be about 1.5 mm. In fixation pin 110 of FIG. 8 and FIG. 9, the diameter of pin shaft 120 may be larger at about 2 mm. Additionally, fixation pin 110 is not limited to the dimensions shown in FIG. 6, FIG. 7, FIG. 8, and FIG. 9. These dimensions are exemplary only.

Referring now to FIG. 10, FIG. 11A, FIG. 11B, FIG. 12A, and FIG. 12B is a perspective view, a side view, a cross-sectional view, a top view, and a bottom view, respectively, of an example of fixation screw 130 of NGSF kit 100, in accordance with an embodiment of the invention.

Additionally, FIG. 13 and FIG. 14 show various views showing dimensions of an example of fixation screw 130 of NGSF kit 100. In this example, the overall length of fixation screw 130 may be about 29 mm, the diameter of fixation screw head 132 may be about 4.76 mm, the diameter of screw shank 138 may be about 2.94 mm, the diameter of screw shaft 140 including threads 142 may be about 2.5 mm, and the length of screw shaft 140 including self-tapping screw tip 144 may be about 20 mm. Accordingly, in this example, the diameter of through-hole 156 of surgical sleeve 150 that is designed to receive the screw shank 138—portion of fixation screw 130 may be about 3.0 mm.

Referring now to FIG. 15A, FIG. 15B, FIG. 15C, FIG. 15D, and FIG. 15E is a perspective view, a side view, a cross-sectional view, a top view, and a bottom view, respectively, of an example of surgical sleeve 150 of NGSF kit 100, in accordance with an embodiment of the invention. In this example and referring now to FIG. 15C, the height of sleeve body 152 may be about 3.0 mm and the height of sleeve baseplate 154 may be about 1.0 mm. Accordingly, the overall height of surgical sleeve 150 may be about 4.0 mm. The diameter of sleeve baseplate 154 may be about 5.0 mm, the diameter of sleeve body 152 may be about 4.0 mm, and the diameter of through-hole 156 may be about 3.0 mm. Accordingly, in this example, the diameter of sleeve body 152 may be designed to fit into the original and larger diameter fixation guide hole of the surgical guide. In one example, the fixation guide holes of the surgical guide may be sized to receive the 4 mm-diameter sleeve body 152 of surgical sleeve 150. Additionally, surgical sleeve 150 is not limited to the dimensions shown in FIG. 15C. These dimensions are exemplary only.

Referring now to FIG. 16, FIG. 17A, FIG. 17B, FIG. 18A, and FIG. 18B is a perspective view, a side view, a cross-sectional view, a top view, and a bottom view, respectively, of an example of fixation drill key 160 of NGSF kit 100, in accordance with an embodiment of the invention. In this example and referring now to FIG. 17B and FIG. 18A, the height of drill key body 162 may be about 2.0 mm and the height of drill key shank 166 may be about 4.0 mm. Accordingly, the overall height of fixation drill key 160 may be about 6.0 mm. The diameter of drill key body 162 may be about 5.0 mm, the diameter of drill key shank 166 may be about 2.94 mm, and the diameter of through-hole 168 may be about 1.5 mm. Additionally, drill key arm 164 may have a length of about 24 mm, a height of about 1.5 mm, and a width of about 4.0 mm. Additionally, fixation drill key 160 is not limited to the dimensions shown in FIG. 17B and FIG. 18A. These dimensions are exemplary only.

Referring now to FIG. 19, FIG. 20A, and FIG. 20B is a perspective view, a side view, and a cross-sectional view, respectively, of an example of fixation pin 110 engaged with surgical sleeve 150 of NGSF kit 100. For example, surgical sleeve 150 may be installed on pin shaft 120 of fixation pin 110 such that the pin shank 116—portion of fixation pin 110 is fitted within through-hole 156 of surgical sleeve 150 and with sleeve baseplate 154 of surgical sleeve 150 resting against baseplate 118 of fixation pin 110.

Referring now to FIG. 21, FIG. 22A, and FIG. 22B is a perspective view, a side view, and a cross-sectional view, respectively, of an example of fixation screw 130 engaged with surgical sleeve 150 of NGSF kit 100. For example, surgical sleeve 150 may be installed on screw shaft 140 of fixation screw 130 such that the screw shank 138—portion of fixation screw 130 is fitted within through-hole 156 of surgical sleeve 150 and with sleeve baseplate 154 of surgical sleeve 150 resting against screw end 136 of fixation screw head 132 of fixation screw 130.

Referring now to FIG. 23, FIG. 24, and FIG. 25 is a perspective view, a side view, and a cross-sectional view, respectively, of an example of surgical sleeve 150, fixation drill key 160, and fixation drill bit 170 of NGSF kit 100 assembled together, in accordance with an embodiment of the invention. Further, FIG. 26 shows another side view and cross-sectional view of an example of surgical sleeve 150, fixation drill key 160, and fixation drill bit 170 of NGSF kit 100 assembled together. Here, fixation drill key 160 is first fitted onto fixation drill bit 170. Then, fixation drill bit 170 with drill key shank 166 of fixation drill key 160 is fitted into through-hole 156 of surgical sleeve 150.

Referring now to FIG. 27 is a flow diagram of an example of a method 200 of using NGSF kit 100 as described hereinabove with reference to FIG. 1A through FIG. 25. Method 200 may occur in the process of performing intraoral guided surgery procedures, such as, but not limited to, bone fixated (bone touching/contacting) guide-assisted surgical procedures. NGSF kit 100 and method 200 may be used to provide a secure, temporary, fixation of surgical guides to the buccal surface on the maxillary and mandibular arch. The fixation will commonly be used in a bicortical or unicortical application. Further, method steps 220 through 255 of method 200 may be repeated for each fixation pin 110 and/or fixation screw 130 used in the procedure. Method 200 may include, but is not limited to, the following steps.

At a step 210, the NGSF kit (or system) 100 is provided. For example, NGSF kit 100 that may include fixation pin 110 and/or fixation screw 130, surgical sleeve 150, fixation drill key 160, and fixation drill bit 170, as described hereinabove with reference to FIG. 1A through FIG. 25, may be provided.

At a step 215, intraoral surgical guides are provided and then positioned with respect to subject's mouth. For example, one or more intraoral surgical guides, such as those used in intraoral guided surgery procedures, may be provided. The one or more intraoral surgical guides are provided with surgical sleeves 150 already installed and secured within their fixation guide holes. Then the one or more intraoral surgical guides (not shown) may be positioned with respect to subject's oral cavity.

At a step 220, fixation drill bit 170 is engaged with surgical sleeve 150 of NGSF kit 100 and then the fixation and/or pilot hole is drilled in the oral cavity. For example, fixation drill bit 170 with fixation drill key 160 is engaged with surgical sleeve 150 of NGSF kit 100, as shown, for example, in FIG. 21 through FIG. 25. Then, the fixation and/or pilot hole is drilled in the subject's oral cavity.

At a step 225, fixation drill bit 170 with fixation drill key 160 is removed from surgical sleeve 150 of NGSF kit 100.

At a step 230, fixation pin 110 or fixation screw 130 of NGSF kit 100 is inserted into surgical sleeve 150 of NGSF kit 100. In one example, the surgeon selects the 1.5 mm-shaft fixation pin 110 (see FIG. 6 and FIG. 7). Then, the 1.5 mm-shaft fixation pin 110 may be inserted into surgical sleeve 150 as shown in FIG. 19, FIG. 20A, and FIG. 20B. More specifically, the pin shank 116—portion of fixation pin 110 may be fitted into through-hole 156 of surgical sleeve 150. In another example, fixation screw 130 may be inserted into surgical sleeve 150 as shown in FIG. 21, FIG. 22A, and FIG. 22B. More specifically, the screw shank 138—portion of fixation screw 130 may be fitted into through-hole 156 of surgical sleeve 150.

At a step 235, fixation pin 110 is tapped or fixation screw 130 is turned into the buccal and/or the lingual bone and the procedure continues. For example, the surgeon taps the fixation pin 110 or turns the fixation screw 130 into the subject's buccal and/or the lingual bone and the procedure continues.

At a decision step 240, it is determined whether fixation pin 110 or fixation screw 130 has loosened. For example, at any time during the intraoral guided surgery procedure, the surgeon may notice or determine that the fixation pin 110 or fixation screw 130 has loosened. If fixation pin 110 or fixation screw 130 has not loosened, then method 200 ends. However, if it is determined that fixation pin 110 or fixation screw 130 has loosened, then method 200 may proceed to step 245.

At a step 245, the loose fixation pin 110 or the loose fixation screw 130 of NGSF kit 100 is removed from the bone and from surgical sleeve 150 of NGSF kit 100. For example, the surgeon may extract the loose fixation pin 110 or the loose fixation screw 130 from the subject's bone and remove it from surgical sleeve 150, which is in a fixation guide hole of the surgical guide.

At a step 250, a larger fixation pin 110 or fixation screw 130 of NGSF kit 100 is selected and then inserted into surgical sleeve 150 of NGSF kit 100. For example, the surgeon may select a fixation pin 110 or fixation screw 130 or any other fixation device that is larger than the fixation pin 110 or fixation screw 130 selected in method step 235. For example, if the fixation pin 110 selected in method step 235 is the 1.5 mm-shaft fixation pin 110 (see FIG. 6 and FIG. 7), then here the surgeon may select the 2 mm-shaft fixation pin 110 (see FIG. 8 and FIG. 8), which is then installed in through-hole 156 of surgical sleeve 150.

At a step 255, the larger fixation pin 110 is tapped or larger fixation screw 130 is turned into the buccal and/or the lingual bone. For example, the surgeon taps the larger fixation pin 110 or turns the larger fixation screw 130 into the original hole that was drilled in the subject's buccal and/or the lingual bone and thereby resecures the surgical guide.

In summary and referring now again to FIG. 1A through FIG. 27, the NGSF kit (or system) 100 and method 200 provide mechanisms suitable for use in intraoral guided surgery procedures, such as, but not limited to, bone fixated (bone touching/contacting) guide-assisted surgical procedures. The mechanism may include, for example, a selection of fixation pins 110, a selection of fixation screws 130, the surgical sleeve 150, and the fixation drill bit 170 including the fixation drill key 160.

In one example, the NGSF kit (or system) 100 and method 200 may provide the fixation pin 110 that may include pin head 112, pin shank 116, pin shaft 120 with pin tip 122 and wherein pin shank 116 has a certain diameter and pin shaft 120 has a certain diameter that is smaller than the pin shank 116 diameter and wherein the hole diameter of surgical sleeve 150 is sized to the nominal diameter of pin shank 116, instead of to the nominal diameter of pin shaft 120.

In another example, the NGSF kit (or system) 100 and method 200 may provide the fixation screw 130 that may include fixation screw head 132, screw shank 138, screw shaft 140 with self-tapping screw tip 144 and wherein screw shank 138 has a certain diameter and screw shaft 140 has a certain diameter that is smaller than the screw shank 138 diameter and wherein the hole diameter of surgical sleeve 150 is sized to the nominal diameter of screw shank 138, instead of to the nominal diameter of screw shaft 140.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the subject matter of the present invention. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A navigation-guided surgery fixation (NGSF) system, comprising:
   a. a fixation member for fixating an intraoral surgical guide, the fixation member comprising:
      i. a shank portion; and
      ii. a shaft portion, the shaft portion extending out from an end portion of the shank portion, and wherein the shank portion has a diameter greater than that of the shaft portion;
   b. a sleeve member, wherein the sleeve member comprises a through-hole substantially the same size of the shank portion and configured to receive the shank portion therein;
   c. a fixation drill key, the fixation drill key comprising a through-hole, wherein at least a portion of the fixation drill key is configured to be received within the through-hole of the sleeve member; and
   d. a fixation drill bit, wherein at least a portion of the fixation drill bit is configured to be received through the through-hole of the fixation drill key.

2. The system of claim 1, wherein the fixation member comprises at least one of a fixation pin or a fixation screw.

3. The system of claim 1, wherein the fixation member further comprises:
   a. a head portion at a proximal end of the fixation member;
   b. a baseplate portion spaced apart from the head portion;
   c. a spacer portion disposed between the head portion and the baseplate portion;
   d. a tip portion at a distal end of the shaft portion; and
   wherein the shank portion extends out at its proximal end from a side of the baseplate opposite that of the spacer.

4. The system of claim 1, wherein the sleeve member further comprises:
   a. a sleeve body; and
   b. a sleeve baseplate.

5. The system of claim 4, wherein the sleeve body is configured to fit within a fixation guide hole of the intraoral surgical guide.

6. The system of claim 1, wherein the fixation drill key further comprises:
   a. a drill key body;
   b. a drill key arm extending out perpendicularly from a side of the drill key body; and
   c. a drill key shank extending from a surface of the drill key body and substantially perpendicular to the drill key arm, and wherein the through-hole of the fixation drill key extends through both the drill key body and the drill key shank.

7. The system of claim 1, wherein the fixation drill bit comprises:
   a. a drill bit shank; and
   b. a drill bit, the drill bit extending out from the drill bit shank, wherein the drill bit portion is configured to be at least partially received through the sleeve member through-hole and the fixation drill key through-hole.

8. A navigation-guided surgery fixation (NGSF) kit, comprising:
   a. a plurality of fixation members, each comprising a shank portion and a shaft portion extending out from an end portion of the shank portion, wherein the shank portions of all of the plurality of fixation members have a same diameter which is greater than a diameter of any one of the shaft portions of the plurality of fixation members, and wherein the shaft portions of one or more of the plurality of fixation members have differing diameters from one another; and
   b. a sleeve member, wherein the sleeve member comprises a through-hole having a diameter substantially the same as that of the shank portion of the plurality of fixation members and is configured to receive the shank portion of the plurality of fixation members therein.

9. The kit of claim 8, wherein the fixation member comprises at least one of a fixation pin or a fixation screw.

10. The kit of claim 8, further comprising:
   a. a fixation drill key, the fixation drill key comprising a through-hole, wherein at least a portion of the fixation drill key is configured to be received within the through-hole of the sleeve member; and
   b. a fixation drill bit, wherein at least a portion of the fixation drill bit is configured to be received through the through-hole of the fixation drill key.

\* \* \* \* \*